United States Patent
Morejohn et al.

(10) Patent No.: US 12,285,173 B2
(45) Date of Patent: Apr. 29, 2025

(54) SYSTEMS AND METHODS FOR LEFT ATRIAL APPENDAGE CLOSURE

(71) Applicant: AtriCure, Inc., Mason, OH (US)

(72) Inventors: Dwight P. Morejohn, Davis, CA (US); Tamer Ibrahim, Danville, CA (US); Michael J. Banchieri, Discovery Bay, CA (US); Ara Stephanian, Davis, CA (US); Brian Flores, Castro Valley, CA (US)

(73) Assignee: AtriCure, Inc., Mason, OH (US)

( * ) Notice: Subject to any disclaimer, the term of this patent is extended or adjusted under 35 U.S.C. 154(b) by 266 days.

(21) Appl. No.: 17/658,640

(22) Filed: Apr. 8, 2022

(65) Prior Publication Data

US 2022/0346796 A1    Nov. 3, 2022

Related U.S. Application Data

(63) Continuation of application No. 14/582,868, filed on Dec. 24, 2014, now Pat. No. 11,324,510.
(Continued)

(51) Int. Cl.
*A61B 17/12* (2006.01)
*A61B 1/04* (2006.01)
(Continued)

(52) U.S. Cl.
CPC .......... *A61B 17/12013* (2013.01); *A61B 1/04* (2013.01); *A61B 2017/00243* (2013.01);
(Continued)

(58) Field of Classification Search
CPC .............. A61B 17/12013; A61B 90/37; A61B 17/0482; A61B 2017/306;
(Continued)

(56) References Cited

U.S. PATENT DOCUMENTS

| 5,281,238 A | 1/1994 | Chin et al. |
| 5,908,429 A | 6/1999 | Yoon |

(Continued)

FOREIGN PATENT DOCUMENTS

| CN | 102573665 | 7/2012 |
| CN | 102612345 | 7/2012 |
| WO | WO 2008/121278 | 10/2008 |

OTHER PUBLICATIONS

Contractor, T., et al., "Left Atrial Appendage Closure in Atrial Fibrillation: A World without Anticoagulation?" SAGE-Hindawi Access to Research, Cardiology Research and Practice, Feb. 1, 2011, vol. 2011, Article ID 752808, 7 pages.

*Primary Examiner* — Darwin P Erezo
*Assistant Examiner* — Christina C Lauer
(74) *Attorney, Agent, or Firm* — Levine Bagade Han LLP

(57) ABSTRACT

Embodiments of the present invention encompass systems and methods for delivering ligatures to anatomical features of a patient. Exemplary ligature delivery systems for use in delivering a ligature to a left atrial appendage ligature include an elongate support mechanism having a proximal portion and a distal portion, a flexible hoop assembly, and a cinchable constriction member. The flexible hoop assembly can be coupled with the distal portion of the elongate support mechanism, and can include a support body coupled with a support frame. The support frame can be biased to hold the support body in a trailing configuration, whereby a free portion of the support body is disposed proximal to the distal portion of the elongate support mechanism. The support frame of the flexible hoop assembly can be coupled with the distal portion of the elongate support mechanism. The
(Continued)

support body can be configured to support the cinchable constriction member and a loop of the left atrial appendage ligature.

14 Claims, 16 Drawing Sheets

Related U.S. Application Data

(60) Provisional application No. 61/921,985, filed on Dec. 30, 2013.

(51) Int. Cl.
| | |
|---|---|
| A61B 17/00 | (2006.01) |
| A61B 17/02 | (2006.01) |
| A61B 17/04 | (2006.01) |
| A61B 17/30 | (2006.01) |
| A61B 90/00 | (2016.01) |

(52) U.S. Cl.
CPC ............. *A61B 2017/0243* (2013.01); *A61B 2017/0475* (2013.01); *A61B 17/0482* (2013.01); *A61B 2017/306* (2013.01); *A61B 90/37* (2016.02)

(58) Field of Classification Search
CPC ...... A61B 2017/0475; A61B 17/12009; A61B 17/12; A61B 17/12099; A61B 17/12122; A61B 17/0057
See application file for complete search history.

(56) References Cited

U.S. PATENT DOCUMENTS

| | | |
|---|---|---|
| 5,984,917 A | 11/1999 | Fleischman et al. |
| 6,379,366 B1 | 4/2002 | Fleischman et al. |
| 6,610,072 B1 | 8/2003 | Christy et al. |
| 7,806,894 B1 | 10/2010 | Rosenblatt et al. |
| 8,715,302 B2 | 5/2014 | Ibrahim et al. |
| 9,498,206 B2 | 11/2016 | Fung et al. |
| 11,324,510 B2* | 5/2022 | Morejohn ........ A61B 17/12013 |
| 2004/0102804 A1 | 5/2004 | Chin |
| 2004/0260273 A1 | 12/2004 | Wan |
| 2005/0149069 A1 | 7/2005 | Bertolero et al. |
| 2006/0020271 A1* | 1/2006 | Stewart ............ A61B 17/12013 606/139 |
| 2006/0020336 A1 | 1/2006 | Liddicoat |
| 2006/0253129 A1 | 11/2006 | Liddicoat |
| 2008/0243183 A1* | 10/2008 | Miller ................ A61B 17/0469 606/228 |
| 2008/0294175 A1* | 11/2008 | Bardsley ............ A61B 17/1285 606/113 |
| 2008/0312664 A1 | 12/2008 | Bardsley et al. |
| 2010/0204716 A1 | 8/2010 | Stewart et al. |
| 2011/0276075 A1 | 11/2011 | Fung et al. |
| 2012/0323262 A1* | 12/2012 | Ibrahim ........... A61B 17/12013 606/144 |
| 2013/0144311 A1 | 6/2013 | Fung et al. |
| 2014/0336676 A1 | 11/2014 | Pana et al. |
| 2015/0182225 A1 | 7/2015 | Morejohn et al. |

* cited by examiner

MIS (MINIMALLY INVASIVE SURGERY)

SYSTEMS AND METHODS FOR LEFT ATRIAL APPENDAGE CLOSURE

CROSS-REFERENCE TO RELATED APPLICATIONS

This application is a continuation of U.S. patent application Ser. No. 14/582,868 filed Dec. 24, 2014, now U.S. Pat. No. 11,324,510, which claims priority to U.S. Provisional Patent Application No. 61/921,985 filed Dec. 30, 2013. This application is also related to U.S. patent application Ser. No. 13/524,891 filed Jun. 15, 2012. The content of each of the above filings is incorporated herein by reference.

BACKGROUND OF THE INVENTION

Embodiments of the present invention relate to systems and methods for closing anatomical structures of a patient. Particular embodiments related to techniques for closing the left atrial appendage of a patient.

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be underprescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

One possible complication as a result of AF is that clots from the left atrial appendage may embolize and cause harm to the patient. For example, dislodged clots can form emboli that lead to ischemic damage to a person's brain, kidneys, or other organs. Although left atrial appendage closure devices and techniques are currently available and provide real benefits to patients in need thereof, significant advances may still be made to provide improved systems and methods for treating the left atrial appendage. Embodiments of the present invention provide solutions and answers to at least some of these outstanding needs.

BRIEF SUMMARY OF THE INVENTION

Embodiments of the present invention encompass devices and methods for treating an anatomical feature, such as a left atrial appendage, of a patient during a surgical procedure. Exemplary techniques include delivering a looped suture to the appendage, using a device having a trailing hoop configuration. Such devices are well suited for use in minimally invasive procedures. In some instances, the diameter of the device can be 1.5 inches or less. In operation, a surgeon can accurately and efficiently drag a hoop assembly of the device to a desired location within the patient, and use the device to deliver a suture to the patient anatomy.

In one aspect, embodiments of the present invention encompass systems and methods for use in delivering a ligature to an anatomical feature of a patient. For example, a ligature delivery system for administering a left atrial appendage ligature to the left atrial appendage may include an elongate support mechanism having a proximal portion and a distal portion, a flexible hoop assembly, and a cinchable constriction member. In some cases, the flexible hoop assembly can be coupled with the distal portion of the elongate support mechanism. In some cases, the flexible hoop assembly can include a support body coupled with a support frame. In some cases, the support frame can be biased to hold the support body in a trailing configuration, such that a free portion of the support body is disposed proximal to the distal portion of the elongate support mechanism. In some cases, the support frame of the flexible hoop assembly can be coupled with the distal portion of the elongate support mechanism. In some cases, the support body can be configured to support the cinchable constriction member and a loop of the left atrial appendage ligature. According to some embodiments, a ligature delivery system can further include a constriction member control mechanism that cinches the cinchable constriction member about the left atrial appendage. According to some embodiments, a ligature delivery system can further include a ligature control mechanism that cinches the left atrial appendage ligature about the left atrial appendage. According to some embodiments, a ligature delivery system can further include a deflector body that pivots relative to the elongate support mechanism. In some cases, the support frame of the flexible hoop assembly can be coupled with the distal portion of the elongate support mechanism via the deflector body. According to some embodiments, a ligature delivery system can further include a deflection control mechanism in operative association with the deflector body, such that actuation of the deflection control mechanism causes the deflector body to pivot relative to the elongate support mechanism. According to some embodiments, a ligature delivery system can further include a lumen that is adapted to receive a visualization mechanism.

In another aspect, embodiments of the present invention encompass methods of delivering a ligature loop to a left atrial appendage of a patient. Exemplary methods may include advancing an elongate support mechanism of a ligature delivery system toward the left atrial appendage of the patient, where the ligature delivery system includes a flexible hoop assembly coupled with the distal portion of the elongate support mechanism, and the flexible hoop assembly is disposed in a trailing configuration. In some cases, methods may include cinching a cinchable constriction member about the left atrial appendage, so as to constrict the left atrial appendage. In some cases, methods may include delivering the ligature loop from the flexible hoop assembly to the constricted left atrial appendage. In some instances, the step of cinching the cinchable constriction member about the left atrial appendage includes actuating a constriction member control mechanism of the ligature delivery system. According to some embodiments, the flexible hoop assembly includes a support body coupled with a support frame, and the support frame is biased to hold the flexible hoop assembly in the trailing configuration whereby a free portion of the support body is disposed proximal to the distal portion of the elongate support mechanism. In some instances, the flexible hoop assembly is coupled with the distal portion of the elongate support mechanism via a deflector body, and methods can further include pivoting the deflector body of the ligature delivery system relative to the elongate support mechanism. In some instances, the ligature delivery system includes a deflection control mechanism in operative association with the deflector body, and methods can further include actuating the deflection control mechanism to cause the deflector body to pivot relative to the elongate support mechanism. In some instances, the ligature delivery system includes a lumen that receives a visualization mechanism, and methods can further include visualizing the left atrial appendage with the visualization mechanism. In some instances, the ligature delivery system includes a suction mechanism, and methods can further include transmitting suction from a suction source to the left atrial appendage of the patient. In some cases, the suction mechanism includes a suction pod, and methods can further include drawing tissue of the left atrial appendage of the patient into the suction pod.

In still another aspect, embodiments of the present invention encompass ligature delivery systems for use with a left atrial appendage ligature. Exemplary ligature delivery systems can include an elongate support mechanism, and a flexible hoop assembly coupled with the elongate support mechanism. The flexible hoop assembly can be biased in a trailing configuration whereby a free portion of the flexible hoop assembly is disposed proximal to a distal portion of the elongate support mechanism. Exemplary ligature delivery systems can also include a cinchable constriction member. In some instances, the flexible hoop assembly is configured to support the cinchable constriction member and a loop of the left atrial appendage ligature. According to some embodiments, the flexible hoop assembly includes a groove configured to receive the cinchable constriction member. In some instances, a portion of the groove is defined by a flap that collapses flexibly in response to a cinching force applied by the cinchable constriction member. According to some embodiments, the flexible hoop assembly includes a channel configured to receive the loop of the left atrial appendage ligature. In some instances, a portion of the channel is defined by a flap that collapses flexibly in response to a cinching force applied by the loop of the left atrial appendage ligature. In some cases, ligature delivery systems can further include a suction mechanism configured to transmit suction from a suction source to a left atrial appendage of a patient.

For a fuller understanding of the nature and advantages of the present invention, reference should be had to the ensuing detailed description taken in conjunction with the accompanying drawings.

DETAILED DESCRIPTION OF THE INVENTION

Figure 1:
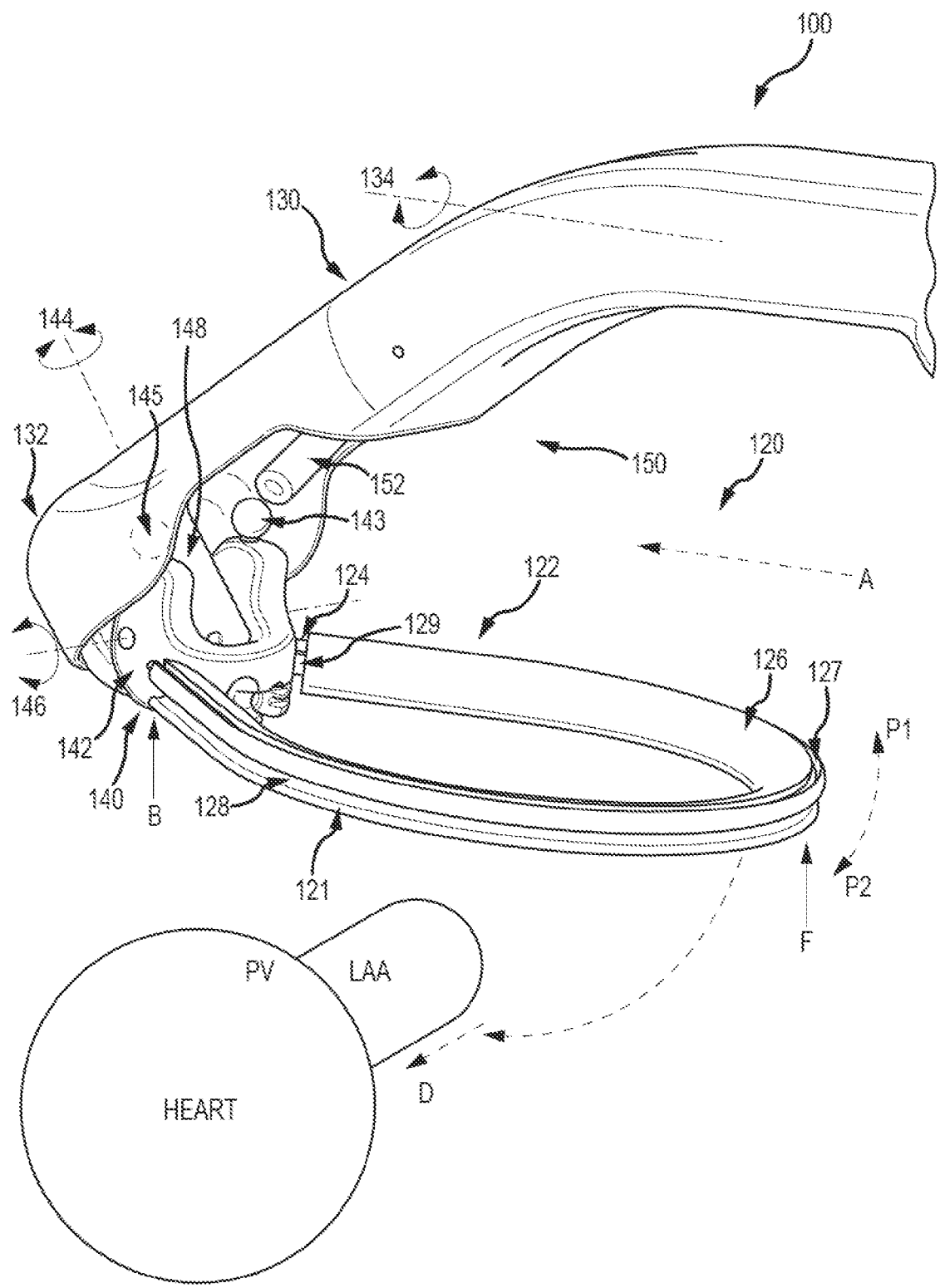
FIG. 1 depicts aspects of a ligature delivery system according to embodiments of the present invention.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments of the present devices provide delivery systems and methods for applying ligatures or sutures to anatomical features of a patient. In some cases, delivery systems and methods can be used with a pre-fabricated ligature assembly or pre-knotted suture thread loop. For example, a ligature assembly or snare apparatus may include a suture or thread that is tied with a one-way knot or hangman's noose, or that is otherwise configured with a one-way control mechanism such as a ratchet. The knot or ratchet mechanism may be held by a distal feature of a delivery system, such that as the operator draws the proximal tail thread portion proximally, the knot or ratchet remains snug against the distal feature as a looped portion of the thread distal to the knot becomes cinched. In this way, the surgeon or user can apply opposing forces to the thread knot and the proximal thread tail, so as to tighten the thread loop about an anatomical feature such as the left atrial appendage. Typically, the ligature assembly is provided as a single-use device.

Ligature delivery device systems and methods disclosed herein can be used with such ligature assemblies so as to provide an efficient and effective approach for delivering looped suture thread to anatomical features of the patient. Such techniques allow the user or surgeon to easily maneuver the distal thread loop about the patient's anatomy, and to control the placement of the distal thread loop as desired. What is more, the present systems and methods may allow the surgeon or operator to firmly cinch the thread loop about the patient's anatomy, without cutting into the patient's tissue. Hence, for example, the present techniques are well suited for use in a minimally invasive approach.

Embodiments of the present invention provide systems and methods for performing epicardial closure of the left atrial appendage. Such systems and methods can be used through any desired surgical access modality, including without limitation sternotomy, left or right thoracotomy, and other procedures as discussed elsewhere herein.

Exemplary systems may include a grasping means or suction member that can be used to adhere to tissue and extend the appendage, so that a closure means or occlusive device can be delivered to the appendage base. Exemplary embodiments provide mechanically simple, user friendly devices, which can be used to apply any of a variety of ligature assemblies or closure means to patient tissue, which are easy to load and reload with such ligature assemblies, and which can be used to efficiently deliver a ligature suture to the tissue (e.g. base of left atrial appendage) while as the same time protecting the tissue from potential cutting effects that may otherwise occur when tightening a ligature thread about the tissue.

Turning now to the drawings, FIG. 1 depicts aspects of an exemplary ligature delivery system 100 according to embodiments of the present invention. As shown here, the system 100 include a thread delivery mechanism 120 having a hoop assembly 122. The hoop assembly 122, in turn, includes a support body 126 and a support frame 124. In some cases, the support body 126 can be provided as an extruded silicone member. In some cases, the support frame or backbone 124 can be provided as a nitinol wire. The support body and/or frame can be referred to as a trailing hoop mechanism. The support body 126 can include a recess or lumen 127 that receives or houses the support frame 124. Further, the support body 126 can include a recess or channel 128 that receives a constriction member 129, such as a cinchable teflon or teflon-coated loop. The recess, groove, or channel 128 can extend along the length of the support body 126.

The support body 126 or hoop can be supported by the frame or backbone 124, and in turn the suture threads and constriction member 129 can be supported by the support body 126. As discussed elsewhere herein, the backbone 124, which may be provided as a nitinol wire, can be anchored to the deflector body 142 or some other rotatable or fixed feature of the system 100, and the support body 126, which may be provided as a silicone extrusion or casing having a particular cross-sectional shape, can house or support the constriction member 129 and one or more sutures. According to some embodiments, backbone 124 may include stainless steel or other similar materials, including shape-memory materials. For example, the backbone member can include a material which bends upon the application of force, without yielding, and resumes its original shape when the applied force is removed. That is, the bending action does not introduce deformities into the backbone member. According to some embodiments, the support body 126 can include materials such as silicone, polyurethane, and the like.

In use, when the constriction member 129 is cinched or constricted, it can slide off of or be deployed by the support body 126, for example as a flap or edge 121 of the body 126 folds or collapses flexibly in response to the cinching force or action of the constriction member 129. Hence, the flap or edge 121 can provide a shelf or guide for the constriction member or cable 129. The constriction member 129 can be tightened down as desired about the anatomical feature (e.g. left atrial appendage), and due to the size or dimension of the constriction member 129, the cinching force does not cause the constriction member 129 to slice into or cause trauma to the anatomical tissue. The constriction member 129 can be cinched to any desired degree, so as to squeeze the tissue into a tourniqueted position. When the constriction member 129 is in the desired position about the anatomical feature, one or more sutures or ligatures can be delivered to the anatomical feature. Typically, delivery of the suture does not involve compressing tissue with the suture itself, because the tissue is already in a compressed configuration due to the presence of the cinched constriction member 129. After the suture is placed as desired, the constriction member 129 can be loosened and removed from the anatomical feature, leaving the suture in place. The system 100 can then be retracted from the patient.

According to some embodiments, the constriction member 129 is provided as a teflon coated cinchable cable, that can be received by or positioned in a slot or recess 127 of the support body 126. As discussed elsewhere here, the support body can be configured to hold or support one or more ligature threads. The support frame 124 can provide a degree of flexibility to the hoop assembly 122, and can also impart or transmit an amount of force to be applied via the hoop assembly 122.

According to some embodiments, the ligature delivery system 100 may also include a constriction control mechanism that can operate to cinch or constrict the constriction member 129 about an anatomical feature, such as the left atrial appendage of a patient. The constriction control mechanism may also operate to loosen the constriction member from the anatomical feature.

According to some embodiments, the ligature delivery system 100 may also include a support mechanism 130 in operative association with the thread delivery mechanism 120. As discussed elsewhere herein, the support mechanism 130 may have a first engagement assembly that receives one or more ligature assemblies, and a second engagement assembly coupled with the cinch control mechanism.

As shown here, the ligature delivery system 100 may also include a deflector assembly 140 having a deflector body 142 that pivots relative to the support mechanism 130. Deflector assembly 140 can also include a linkage body 148 that pivots relative to the support mechanism 130. As discussed elsewhere herein, the deflector body 142 can also include features which interface with or hold or support one or more ligature threads. The deflector body or rotatable head 142 can rotate about a first axis 144 and/or a second axis 146. The deflector body 142 can be provided as a sub-distal deflector body, in that the deflector body 142 can be disposed on the delivery system 100 at a position that is proximal to a distal portion 132 of the support mechanism 130, or that is proximal to a more distal portion of some other aspect of the system. As shown here, the support frame 124 of the hoop assembly 122 can be anchored or fixed to the deflector body 142, so that movement of the deflector body 142 can be transmitted to the hoop assembly 122. In some cases, the support frame or backbone 124 can operate to hold the support body 126 in a desired configuration or shape.

According to some embodiments, the ligature delivery system 100 can also include a deflection control mechanism that is coupled with the deflector assembly 140, and that causes the deflector body 142 of the deflector assembly 140 to pivot relative to the support mechanism 130. A deflection control mechanism may include for example, a joystick control assembly that operates to rotate the deflector body 142 about axis 144 and/or 146. The deflection control mechanism 150 may also include two control rods, where a first control rod 152 is configured to couple with a first ball 143 of the deflector body, and a second control rod (not shown in FIG. 1) is configured to couple with a second ball 145 of the deflector body. The control or push/pull rods can be used to rotate the deflector body 142 into a desired position. In this sense, a first ball 143 and a corresponding rod 152 having a socket for rotatably receiving the ball can form part of a joint. Movement of the rods can effect movement of the deflector body 142 and consequently can effect movement of the hoop assembly 122. For example, when the rods are pushed forward in a distal direction, the deflector body 142 can pivot upward (e.g. about axis 146) so as to draw the free portion F of the hoop assembly 122 in a similar upward fashion toward the support mechanism 130 as indicated by arrow P1. Conversely, when the rods are pulled backward in a proximal direction, the deflector body 142 can pivot downward (e.g. about axis 146) so as to draw the free portion F of the hoop assembly 122 in a similar downward fashion away from the support mechanism 130 as indicated by arrow P2.

The deflector body 142 and linkage body 148 can be coupled together with a pin or other pivot mechanism, so as to provide such pivoting movements. In this way, the deflector body 142 can rotate about axis 146 in a pitch motion. The rods can be disposed along the length of the support mechanism 130, and by manipulating or moving the rods, the deflector body 142 can be moved in various degrees of freedom or throughout a range of motion. In some cases, on rod can be pulled and the other rod can be pushed, so as to rotate the deflector body 142, and in turn the linkage body 148, about the axis 144 in a yaw motion. The cylinder or linkage body 148 can be pivotally attached with the support mechanism 130 to facilitate or enable such rotation, and the support mechanism 130 or a portion thereof can operate as a third body or link in a mechanical linkage (e.g. in combination with the linkage body 148 and the deflector body 142). The linkage body 148 can provide an intermediate linkage member between the support mechanism 130 and the deflector body 142. Control of the rods can effect fluid movement of the deflector body 142 and the hoop assembly 122, with pitch and/or yaw movements. In some cases, movement of the deflector body 142 can operate to generate or apply force from the hoop assembly 122 against the patient tissue. Optionally, such force can be combined with force applied through general movement of the support mechanism 130.

As shown here, the first and second axes 144, 146 of movement allow an operator to rotate the deflector body 142, and hence the hoop assembly 122, in an up and down manner (pitch) with regard to axis 146, and in a side to side matter (yaw) with regard to axis 144. In some cases, the operator can maneuver the system 100 so as to rotate the support mechanism 130 about a long axis 134 (roll). Roll can be achieved by either rotating the system as a whole, or by implementing an integrated rotating mechanism to provide such roll.

A deflector assembly 140 can include any desired number of links or linkage bodies. The configuration and/or number of such links, and the configuration and/or number of joints between such links, can determine the range of angles or positions throughout which the hoop assembly 122 can be maneuvered, for example by operating a handle or joystick of the ligature delivery system 100. The deflector assembly 140 can be configured to enable an operator to move the deflector body 142 and/or hoop assembly 122 to any degree of pitch, yaw, and/or roll as desired.

In operation, the ligature delivery system 100 can be used to deliver one or more ligature loops or pre-tied sutures to an anatomical feature of a patient. For example, a surgeon or operator can use the ligature delivery system 100 to deliver a suture to the thymus of a patient, to a polyp of a patient, to the appendix of a patient, to the left atrial appendage of a patient, and the like.

In some embodiments, the circumference or area of a hoop defined by the support body 126 and the deflector body 142 is not reduced during administration of a suture to the patient. In contrast, the circumference of the constriction member 129 can be reduced when cinching or constricting the constriction member 129 onto the body appendage or anatomy.

As discussed elsewhere herein, the ligature delivery system 100 can be introduced into a patient's body in a variety of ways. For example, the system 100 can be placed into the patient's body via a left side thoracotomy access point, a right side thoracotomy access point, a sternotomy access point, or a sub-xyphoid access point.

The hoop assembly 122 includes a base portion B that is secured with the deflector body 142, and a free portion F that is extended back toward a proximal section of the support mechanism 130. In this way, the free portion F can extend proximally, toward the operator or surgeon. In use, when the ligature delivery system 100 is advanced into or toward the patient anatomy as indicated by arrow A, the base portion B proceeds in advance of the free portion F. Hence, the free portion F can be considered as a trailing portion, and the hoop assembly 122 can be considered as a trailing hoop such that the deflector body 142 (or the distal portion 132 of the support mechanism 130) proceeds in advance of the hoop assembly 122. Hence, for example, when the support mechanism is advanced distally (e.g. as indicated by arrow A), the hoop assembly 122 can be pulled along by the deflector body 142. Relatedly, the hoop assembly 122 can be positioned over an anatomical feature, such as a left atrial appendage LAA of a patient's heart, which is extending toward the operator. For example, during a surgical procedure involving a sternotomy approach, with the patient lying in a supine position, the left atrial appendage LAA can extend away from the patient's head and downward toward the lower extremities. The surgeon or operator can position the free portion F of the hoop assembly 122 beneath the tip of the LAA, place the hoop assembly 122 generally around the LAA, and advance the distal portion 132 of the support mechanism 130 toward the base of the LAA (e.g. toward a pulmonary vein PV), such that the deflector body 142 operates to drag the hoop assembly 122 along the surface of the LAA toward the heart. In this sense, base portion B of the hoop assembly 122 operates as the leading portion of the hoop assembly, and the free portion F of the hoop assembly operates as the trailing portion of the hoop assembly. The base portion B or leading portion of the hoop assembly 122 can be pushed or advanced with force against or toward the heart (e.g. base of LAA) while the free portion F or trailing portion of the hoop assembly 122 is dragged behind as indicated by arrow D. When the hoop assembly 122 is positioned as desired, the constriction member 129 can be deployed and cinched snugly about the left atrial appendage.

It is appreciated that the heart features generally shown in FIG. 1 are provided for illustrative purposes only. In terms of human anatomy, the heart has four chambers, with two atria on the top/back side of the heart, and two ventricles on the bottom/front side of the heart. An atrioventricular groove is at the junction between the atria and the ventricles and extends about a portion of the heart. The left atrial appendage originates on the left atrium adjacent or tangent to the atrioventricular groove on the left side of the heart and can be considered to lean over the atrioventricular groove, overlapping a small portion of the left ventricle. The atrioventricular groove is generally tangent to the left atrial appendage at a point where the left atrial appendage originates. During operation of the ligature delivery system, the hoop assembly can be positioned around the base of the left atrial appendage, such that the hoop assembly, or a portion thereof (e.g. the free portion F), can be placed between the left atrial appendage and the left ventricle, adjacent to the atrioventricular groove. Hence, the atrioventricular groove can provide an anatomical cue or visual target or reference for the surgeon when positioning the hoop assembly. The head or distal portion of the ligature delivery system can be positioned at or on the lateral portion of the left atrial appendage, such that the head or distal portion is directed or oriented toward the base of the left atrial appendage, where the base reflects up from the left pulmonary veins. Hence, the left pulmonary veins can provide an anatomical cue or visual target or reference for the surgeon when positioning the ligature delivery system. Similarly, the surgeon can use an anatomical pocket located anterior to the pulmonary veins as they exit the lungs and attach to the left atrium, inferior to the left pulmonary artery that goes into the lungs just above them, as another anatomical cue or visual target or reference. The surgeon can slide the hoop assembly under the tip of the left atrial appendage, so that the hoop assembly encircles the base of the left atrial appendage, near or in the atrioventricular groove.

The system 100 can be placed into the patient's body via a left side thoracotomy access point, a right side thoracotomy access point, a sternotomy access point, or a sub-xyphoid access point. Any one of these access routes can be used to approach the left atrial appendage.

Figure 1A:
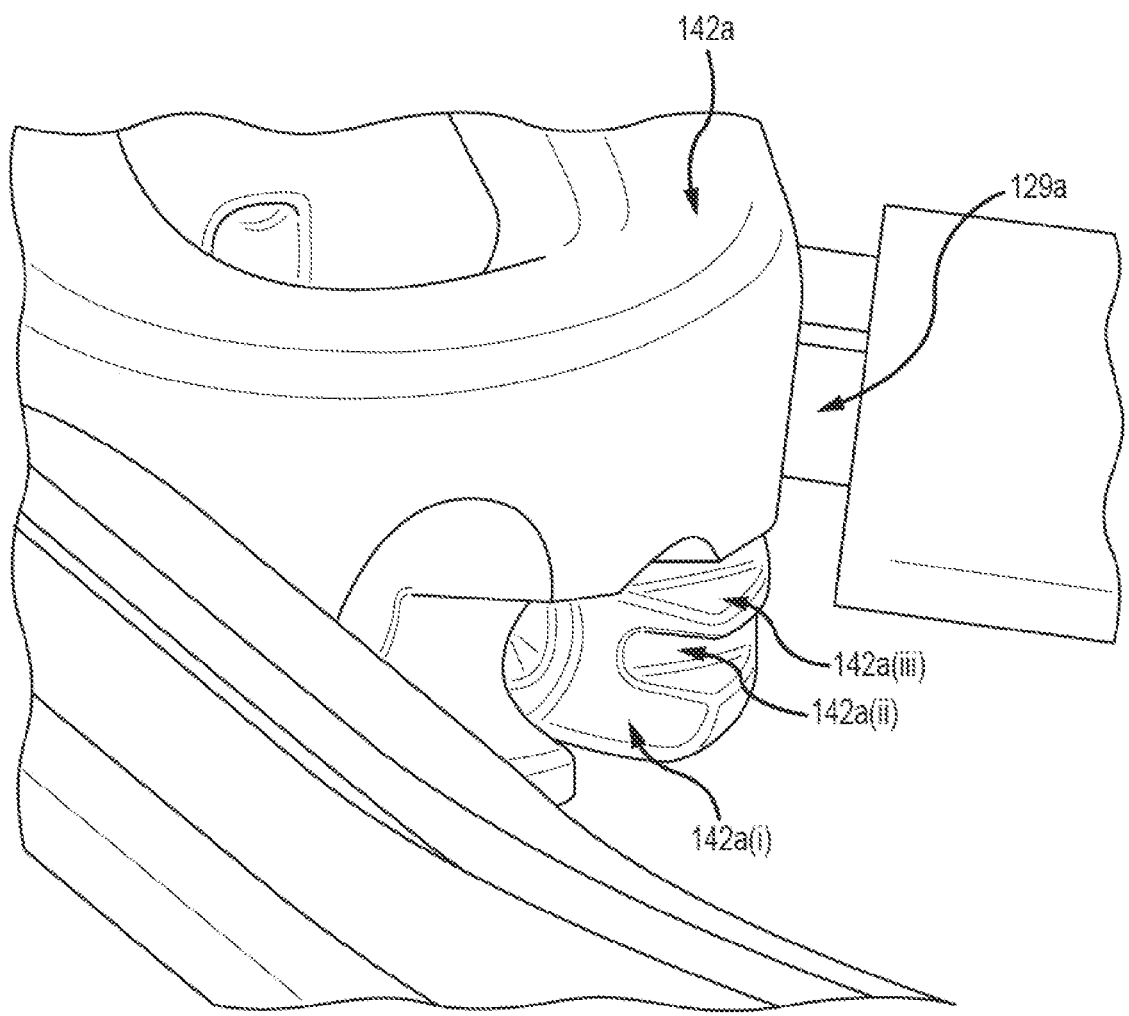
FIGS. 1A, 1B, and 1C depict aspects of ligature delivery systems according to embodiments of the present invention.

As shown in the magnified view of FIG. 1A, a deflector body 142*a* can include a pocket 142*a*(*i*) for holding a knot of a suture (or respective knots of multiple sutures). The deflector body 142*a* can also include grooves or slots 142*a*(*ii*), 142*a*(*iii*) for holding threads of the suture. In use, the sutures can be delivered in a position on the left atrial appendage or anatomical feature which is below the position of the constriction member 129*a*. In this way, the sutures are not trapped against the tissue by the constriction member. The suture positioned in the lower groove 142*a*(*ii*) can be deployed, followed by deployment of the suture positioned in the upper groove 142*a*(*iii*). Hence, the sutures do not become entangled with one another, or with the constriction member.

Figure 1B:
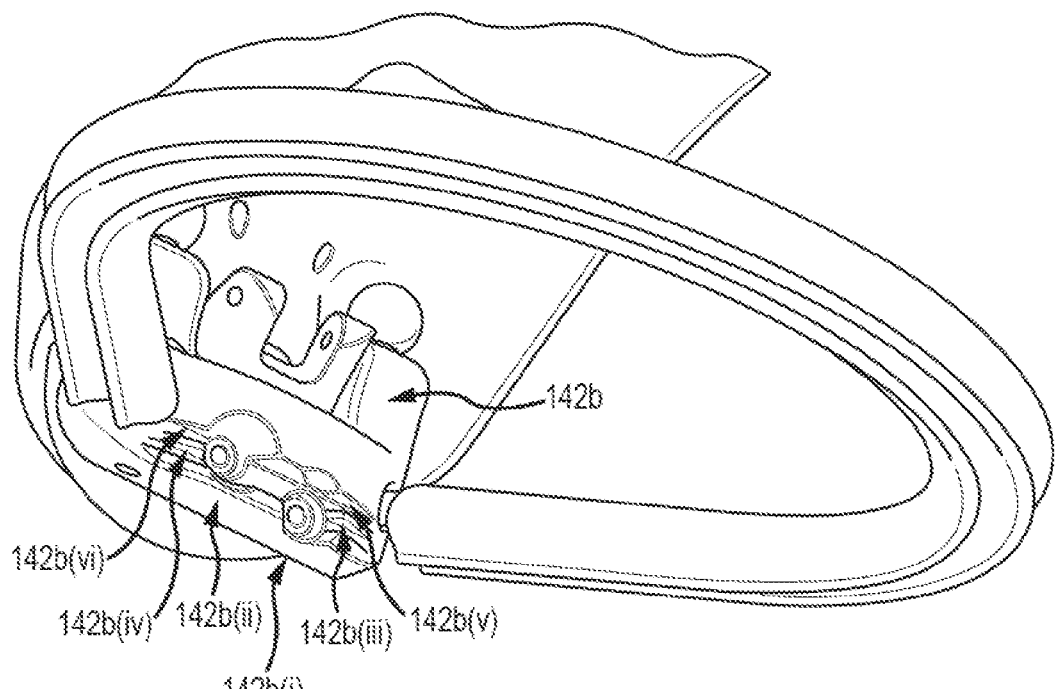

As shown in the magnified view of FIG. 1B depicts, in some embodiments a deflector body 142*b* can include multiple pockets (e.g. pocket 142*b*(*i*) and pocket 142*b*(*ii*) for holding respective knots of multiple sutures). The deflector body 142*b* can also include grooves or slots for holding threads of the sutures. For example, groove or slots 142*b*(*iii*) and 142*b*(*iv*) can hold thread portions of the suture placed at pocket 142*b*(*i*). Similarly, groove or slots 142*b*(*v*) and 142*b*(*vi*) can hold thread portions of the suture placed at pocket 142*b*(*ii*).

In use, the sutures can be delivered in a position on the left atrial appendage or anatomical feature which is below the position of the constriction member. In this way, the sutures are not trapped against the tissue by the constriction member. The suture positioned in the lower pocket and grooves, 142*b*(*i*), 142*b*(*iii*), and 142*b*(*iv*) can be deployed, followed by deployment of the suture positioned in the upper pocket and grooves 142*b*(*ii*), 142*b*(*v*), and 142*b*(*vi*). Hence, the sutures can be deployed sequentially, and do not become entangled with one another, or with the constriction member.

Figure 1C:
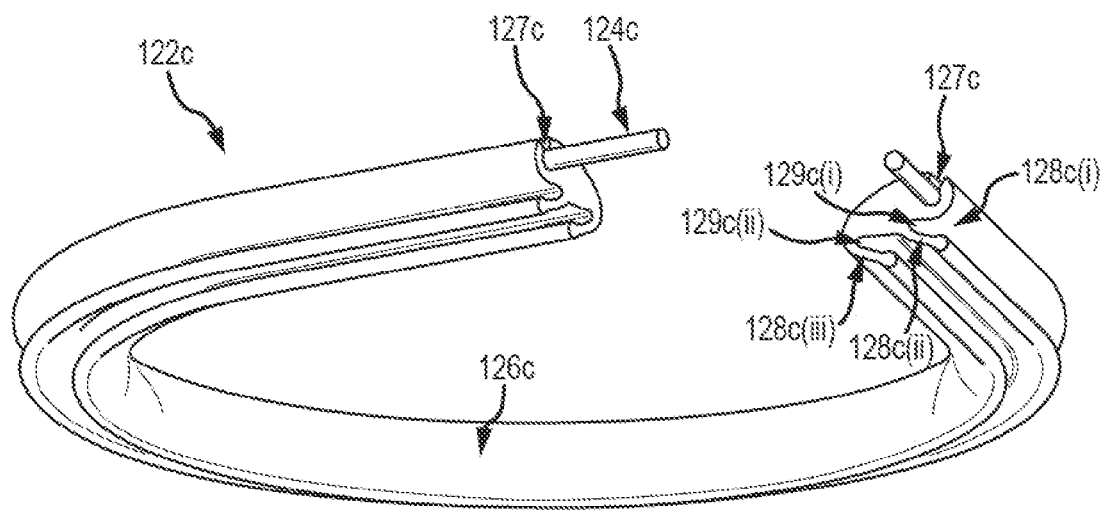

FIG. 1C depicts aspects of an exemplary hoop assembly 122*c*, according to embodiments of the present invention. As shown here, the hoop assembly 122*c* can include a support body 126*c* and a support frame 124*c*. In some cases, the support body 126*c* can be provided as an extruded or cast silicone member. In some cases, the support frame or backbone 124*c* can be provided as a nitinol (nickel titanium) wire. The support body 126*c* can include a recess or lumen 127*c* that receives or houses the support frame 124*c*. In use, a constriction member (e.g. cinchable Teflon or Teflon-coated loop; not shown) can sit freely above or on top of the support body 126*c*, and in a generally coplanar arrangement with the support body.

As shown here, the support body 126*c* includes an upper portion 128*c*(*i*), a first flap 128*c*(*ii*), and a second flap 128*c*(*iii*). The upper portion 128*c*(*i*) and first flap 128*c*(*ii*) define a channel 129*c*(*i*) that receives a thread of a ligature or suture. Similarly, the upper portion 128*c*(*i*), the first flap 128*c*(*ii*), or a combination thereof, along with the second flap 128*c*(*iii*), define a channel 129*c*(*ii*) that receives another thread of a ligature or suture. During delivery of the sutures, the flaps can fold or collapse flexibly in response to the cinching force or action of the sutures.

Figure 2:
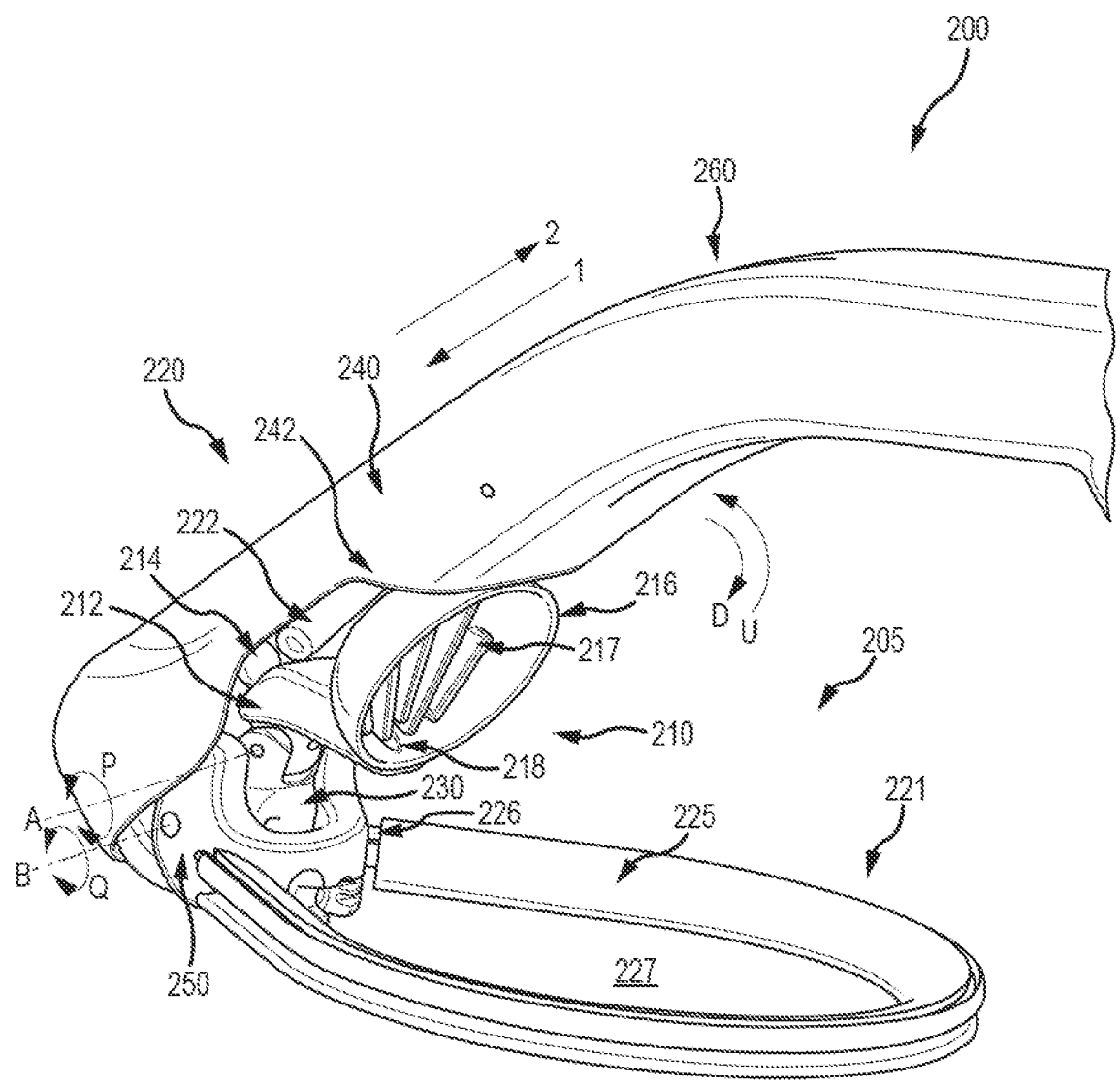
FIG. 2 depicts aspects of a ligature delivery system according to embodiments of the present invention.

FIG. 2 depicts aspects of an exemplary ligature delivery system 200 according to embodiments of the present invention. The system shown here is provided with a trailing hoop and a trailing suction mechanism. Ligature delivery system 200 includes many of the features that are included in the ligature delivery system 100 of FIG. 1. For example, the system 200 can include a thread delivery mechanism 205 having a hoop assembly 221. The ligature delivery system 200 can also include a suction mechanism 210 and associated suction control mechanism 220. The suction mechanism 210 includes a suction pod body 212, a ball 214, a suction pod 216, and a conduit 218 for transmitting suction from a suction source (not shown in FIG. 2) to a patient. In use, suction or low pressure applied to tissue via the suction pod 216 can operate to draw tissue into the interior of the pod 216. When the tissue is secured with the suction pod 216, the system can be operated to move or reposition the suction pod 216, which in turn can operate to move or reposition the tissue.

The suction pod body 212 can be pivotally coupled with a linkage body 230, for example via a pin or pivot mechanism. In this way, the suction pod body 212 can pivot relative to the linkage body 230 about a pivot axis A, as indicated by arrow P. To effect such pivoting, the system can include a control rod 222 pivotally coupled with ball 214 of suction mechanism 210. When control rod 222 is pushed toward a distal direction as indicated by arrow 1, the suction pod can pivot upward or toward the support mechanism shaft 240 (e.g. toward or into a bend or pocket 242 provided by the shaft 240 of the support mechanism), as indicated by arrow U. Conversely, when control rod 222 is pulled toward a proximal direction as indicated by arrow 2, the suction pod can pivot downward or away from the shaft 240 of the support mechanism (e.g. away from or out of the bend or pocket 242 provided by the support mechanism shaft 240), as indicated by arrow D. Hence, pushing on the control rod 222 can cause the suction pod 216 to advance into a tucked away position, away from the hoop assembly 221, and pulling on the control rod 222 can cause the suction pod 216 to move out of the tucked away position, and toward the hoop assembly 221, or even through the hoop assembly 221.

As shown in FIG. 2, the linkage body 230 can be pivotally coupled with the deflector body 250, for example via a pin or pivot mechanism. In this way, the deflector body 250 can pivot relative to the linkage body 230 about a pivot axis B, as indicated by arrow Q. In this sense, the suction pod 216 and the support body 225 of the hoop assembly 221 can each pivot about their own respective pivot axis (e.g. axis A and B, respectively). Relatedly, pivoting of the suction body 216 can be effected by movement of control rod 222, and pivoting of support body 225 can be effected by movement of a separate or independent control mechanism (e.g. including one or more control rods, such as control rod 152 of FIG. 1). In some cases a ligature delivery system will provide a linkage configuration such that the suction body and the support body both pivot about a common axis. The linkage body 230 can be pivotally coupled with the support mechanism 260 or shaft 240 thereof, in a manner similar to the pivotal coupling between linkage body 148 and support mechanism 130 depicted in FIG. 1.

When suction pod 216 is refracted toward shaft 240 or into recess or pocket 242, and support body 225 is also retracted toward shaft 240 of support mechanism 260, the system 200 may provide a low profile configuration. When in a low profile configuration, the system 200 can easily be maneuvered by a physician or operator throughout various locations in the patient anatomy. For example, the system 200 can be placed into the body, and between ribs or other anatomical structures. The support body 225 can be provided as a silicone hoop or member that easily compresses or squeezes, offering little resistance as the system 200 is navigated throughout the patient anatomy. Similarly, the backbone 226, which may include a nitinol material, can also compress and squeeze in a similar way. Once positioned as desired relative to the heart or left atrial appendage (or another desired anatomical target), the hoop assembly can spring open into a wide open shape. The surgeon can operate the system 200 so as to lower or advance the hoop assembly 221 about or toward the left atrial appendage (or other target), and also lower or advance the suction pod 216 toward the left atrial appendage (or other target). The support body 225 can be advanced along the left atrial appendage, so that the appendage is brought into the central aperture 227 of the hoop assembly, and the support body 225 can be placed toward or snugly against the base of the left atrial appendage. The surgeon can administer suction to the left atrial appendage via the suction pod 216, so as to draw or suction left atrial appendage tissue into the interior of the suction pod 216. The suction pod 216 may include one or more ribs or frame members 217, which can operate to prevent the tissue from being suctioned too far into the pod 216, thus avoiding potential damage to the tissue that may otherwise be caused by excessively acute suction forces applied to a small area of tissue. In this way, a large surface area or portion of tissue can be suctioned with the suction pod 216, allowing the surgeon to use the device to effectively maneuver the desired anatomical structures. Put another way, the ribs 217 or standoffs can keep the tissue from moving too far inward into the pod interior, thus avoiding excessive stretching, bruising, damage, or trauma to the tissue. And at the same time, the ribs 217 can allow a large surface area of tissue to remain engaged by the suction pod 216, without diminishing the size of the engaged tissue. For example, if the tissue is suctioned too far into the interior of the pod, the surface area of the tissue disposed within the pod (or otherwise exposed to or in contact with the suction), can be diminished. The ribs 217 can also prevent the tissue from obstructing or sealing the suction conduit 218. Hence, it may be desirable to maintain suction to a large surface area of tissue, and to keep the tissue away from the orifice or suction conduit 218.

In some cases, a sleeve can be placed over the system 200, so as to retain the hoop assembly 221 is a restrained or low profile position. With the hoop assembly 221 so restrained, the operator can maneuver the system 200 within the patient anatomy in a low profile configuration. As discussed elsewhere herein, the support body 225 and backbone 226 are flexible, and hence can passively bend and deform under stress or applied force, and can also resume their original position or shape when the stress or force is no longer applied. Operation of the control rods and deflector body 250 can effect movement of the hoop assembly 221. Hence, for example, the control rods can be operated so as to retract the hoop assembly into a low profile configuration (e.g. such that hoop assembly 221 is brought into apposition with support mechanism 260 or shaft 240), and a sleeve or sheath can be placed over a distal end portion of the system 200, which can result in passive bending of the hoop assembly. The system 200 can then be maneuvered about the patient anatomy, without having the hoop assembly 221 extended to where it can snag on various features of the anatomy. The sheath or sleeve can then be removed, thus allowing the hoop assembly 221 to spring open, and the control rods can then be used to move or pivot the hoop assembly 221 about as desired.

In use, the surgeon or operator can maneuver the system 200 so as to place the support body 225 about the left atrial appendage, for example by placing a portion of the support body under a distal tip or end portion of the left atrial appendage. The suction pod 216 can be contacted with or positioned against the left atrial appendage, and suction can be applied so as to draw the left atrial appendage tissue into or against the suction pod. The control rod 222 can be actuated so as to pivot the suction mechanism 210 about axis A, thus drawing the left atrial appendage further through the support body 225 and toward the support mechanism 260 or shaft 240. Such movement or positioning of the left atrial appendage can allow the surgeon or operator to achieve enhanced visualization of the anatomical features or surface of the left atrial appendage. Because the axes A and B can be closely aligned or in coalignment, and because these axes can be positioned near or at the base of the left atrial appendage, the pivot point(s) of the system 200 features (e.g. suction pod body 212 and/or deflector body 250) can positioned closely to an anatomical flexing or pivoting point of the left atrial appendage (e.g. at or near the base of the LAA), such that movement of the suction pod body 212 and/or deflector body 250 produces a natural movement of the left atrial appendage, without applying undue stress on the appendage itself. Relatedly, the pod 216, which is attached with the free or distal end of the left atrial appendage, moves with a greater degree of freedom. In this way, the left atrial appendage can be maneuvered by the system 200, without damaging the patient tissue.

Often, the left atrial appendage is naturally positioned or resting on the surface of the heart. The left atrial appendage remains somewhat adhered to the surface or curvature of the heart as the heart repeatedly contracts. In some instance, the system 200 can be positioned at the left atrial appendage, and suction can be applied so as to draw the left atrial appendage tissue into or against the suction pod 216, prior to placing the support body 225 about the left atrial appendage. The system 200 can then be maneuvered or positioned so as to place the support body 225 about the left atrial appendage. In some cases, this sequence of steps can be repeated multiple times, so that suction is used to grasp the tip of the left atrial appendage and lift or pull the LAA away from the heart, the support body can be advanced along the LAA toward the base, the suction can be turned off, the support body can be advanced further, and so on. In some cases, it may be desirable to cease the application of suction before advancing the support body more closely to the base of the LAA, so as to avoid producing excessive bending of the LAA. According to some embodiments, the suction pod 216 can be used to raise or maneuver the left atrial appendage as desired, and a scope or viewing instrument can be used to visualize the left atrial appendage or surrounding cardiac tissue (e.g. viewing the base or neck of the LAA).

According to some embodiments, the suction pod 216 can be used to grasp the tip of the left atrial appendage and to maneuver the tip through the support body 225. Suction can then be terminated, and the support body can be advanced further along the LAA, toward the base. While advancing the support body 225 toward the base of the LAA, it may be desirable to pivot the support body slightly back and forth (i.e. toward and away from the support mechanism 260 or shaft 240). When the support body 225 is positioned as desired relative to the left atrial appendage, the surgeon or operator can use the system to deliver one or more constriction members or sutures to the left atrial appendage. Often, following delivery of a suture or constriction member to the left atrial appendage, the surgeon or operator can advance a cutting instrument along the proximal tail of the suture or constriction member, toward the left atrial appendage, and then clip or cut the proximal tail or thread of the suture or constriction member. For example, a curved pair of scissors can be advanced in a distal direction along the proximal thread tail, using the proximal tail as a guide. When the scissors reach the thread knot, the scissors can be moved back proximally, and then used to cut the suture. The severed proximal tail can then be removed from the patient, leaving in place the knot and loop (or cinch) about the base of the LAA.

Hence, as depicted in FIG. 2, embodiments of the present invention encompass ligature delivery systems having a dual axis configuration with a rotatable or pivotable deflector head, with a reverse suction apparatus. The ligature delivery system 200 can operate in a pull mode whereby suction can be used to draw the left atrial appendage toward or through the support body 225, and the construction of the deflector body 250 and suction pod body 212 provide pivotable points that can be positioned at or near the base of the left atrial appendage. The support body 225 can provide a flexible structure that bends during operation of the system. The system can be manufactured to include additional components in a trailing configuration, either attached to the deflector body 250 (e.g. similar to the attachment between the suction pod body 212 and the deflector body 250), or to a specifically designated pivotable base. Trailing configurations such as those embodied by FIG. 2 are uniquely beneficial for placing a loop or hoop structure under an anatomical feature such as the left atrial appendage, using a distal portion of an elongate member or shaft, such as support mechanism 260. For example, it is possible to maneuver the system so that the hoop is drawn or dragged behind the deflector head, as the deflector head is pushed or advanced toward the base of the left atrial appendage, such that the hoop encircles the left atrial appendage. The proximal portion of the hoop can slip under the tip of the left atrial appendage, which is often pointed or oriented toward the operator or proximal end of the device. In this way, the leading head or deflector head can be naturally placed at the base of the left atrial appendage.

Figure 3:
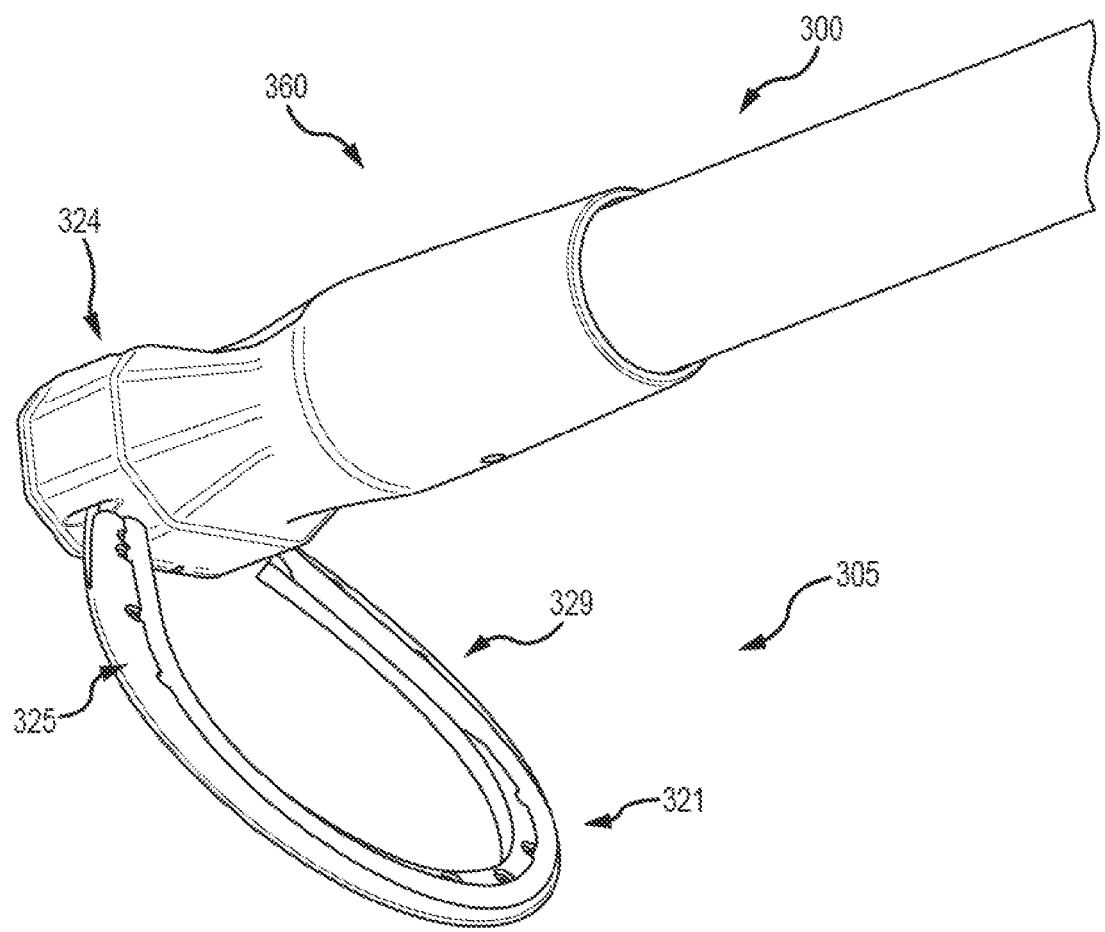
FIG. 3 depicts aspects of a ligature delivery system according to embodiments of the present invention.

FIG. 3 depicts aspects of an exemplary ligature delivery system 300 according to embodiments of the present invention. As shown here, the system 300 includes a support mechanism 360 and a thread delivery mechanism 305 having a hoop assembly 321. The hoop assembly 321 can include a constriction member 329.

Figure 4:
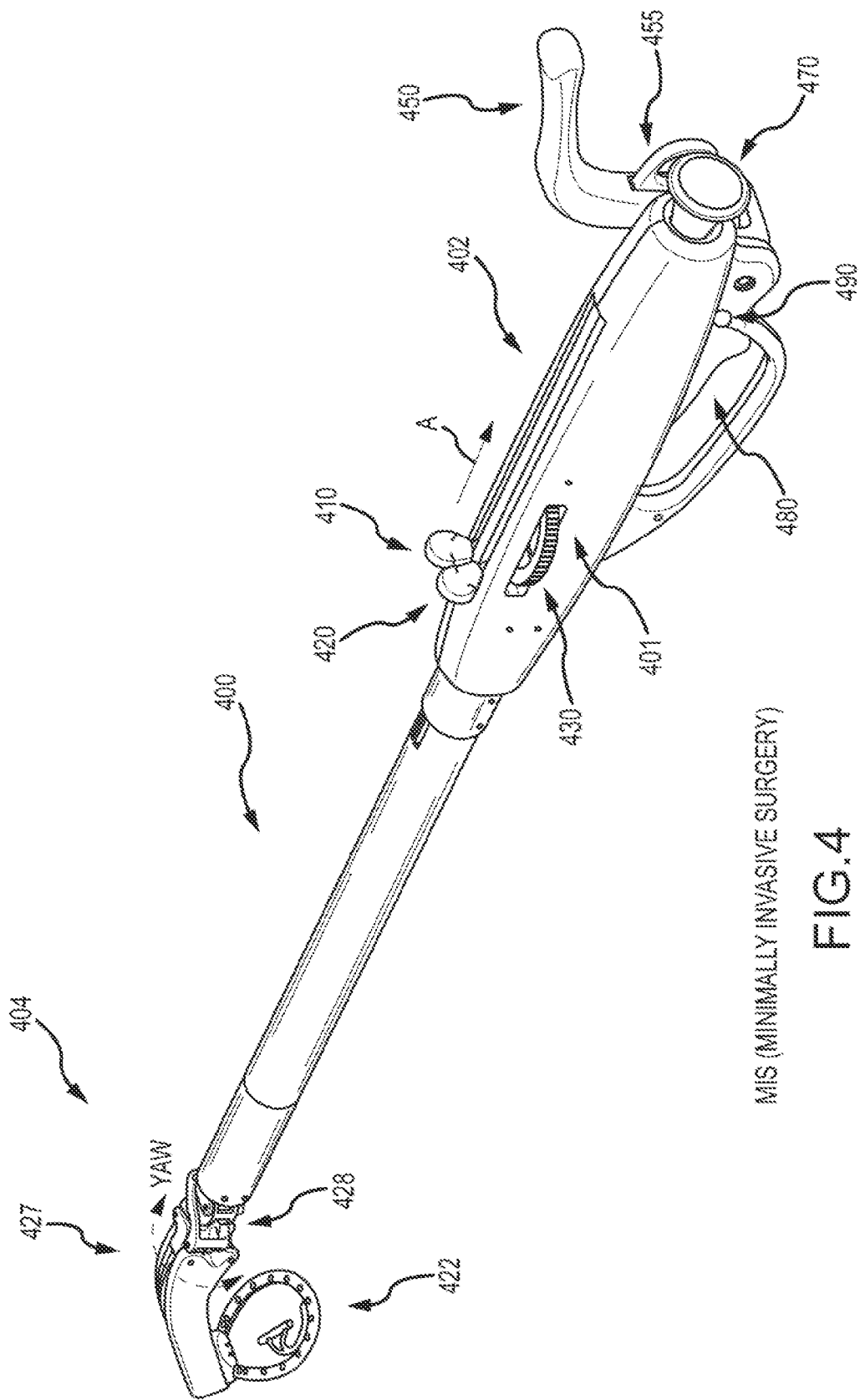
FIG. 4 depicts aspects of a ligature delivery system according to embodiments of the present invention.

According to some embodiments, the system configurations depicted in FIGS. 1 and 2 can be used in subxyphoid and right-side thoracotomy approach surgeries, and the system configurations depicted in FIGS. 3 and 4 can be used in sternotomy and left-side thoracotomy approach surgeries. The systems in FIGS. 3 and 4 generally provide less of a bend, or no bend at all, in the support mechanism as compared with the systems shown in FIGS. 1 and 2. In this way, the systems in FIGS. 3 and 4 present the hoop at a significant angle relative to the support mechanism, to account for the direction at which the surgeon approaches the left atrial appendage.

In some currently known right side thoracotomy procedures, a device is introduced at the patient's right side, and then advanced across the chest, above the lung, through the transverse sinus, around the back of the heart, and to the left side of the heart to reach the left atrial appendage. In some instances, visualization may be difficult with this approach. Once the device is past the transverse sinus, it may be difficult to maneuver the device at the left atrial appendage due to the approach angle. For example, it can be challenging to maneuver a device having a leading or advancing loop so that the leading loop can rotate or pivot in a suitable manner in order to facilitate delivery of a ligature at the left atrial appendage. With a trailing hoop configuration as disclosed herein, however, access to the left atrial appendage via this route can be accomplished efficiently. The trailing hoop provides a sufficiently stiff configuration that can be advanced past the transverse sinus to the left atrial appendage, exiting the transverse sinus on the left side of the heart so as to approach the base of the left atrial appendage. The trailing hoop configuration is also well suited for maneuvering on the inside of the pericardium or pericardial sac. According to some embodiments, a device having trailing hoop configuration can be advanced over the anterior surface of the heart (e.g. instead of advancing across the transverse sinus), inside the pericardium, so as to go over the heart and drop down onto the left atrial appendage. The distal portion of the device (at or near the deflector body) can be advanced toward the base of the left atrial appendage, and the proximal portion of the hoop can slip under the tip of the left atrial appendage. In some cases, in addition to delivering a suture to the left atrial appendage using a ligature delivery system, methods may include providing an ablation treatment to the heart of the patient. For example, a surgeon or operator may perform a minimally invasive cardiac ablation procedure using a COBRA Fusion® ablation system (available from Estech, San Ramon, Calif.). In some cases, both the ligature delivery system and an ablation device can be administered to the patient via the right side. In some cases, an ablation device can be inserted into a right side port, used to perform an ablation treatment, and then withdrawn from the port. A ligature delivery system can then be inserted into the same right side port, used to perform a ligature delivery procedure, and then withdrawn from the port.

Figure 3A:
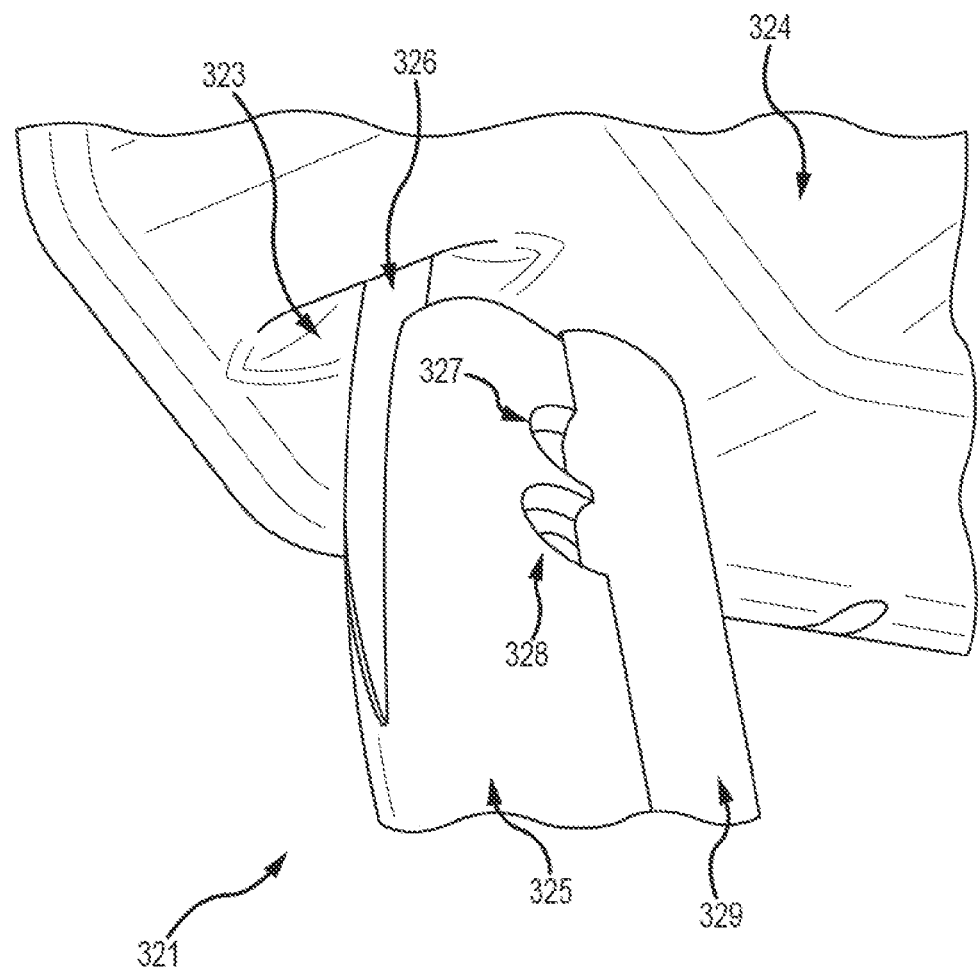
FIG. 3A depicts aspects of a ligature delivery system according to embodiments of the present invention.

As shown in the magnified view of FIG. 3A, the hoop assembly 321 includes a support body 325 and a support frame 326. In some cases, the support body 325 can be provided as an extruded or molded silicone member. In some cases, the support frame or backbone 326 can be provided as a nitinol wire. The support body and/or frame can be referred to as a trailing hoop mechanism. The support body 325 can include a recess or lumen that receives or houses the support frame 326. Further, the support body 325 can include a recess or channel that receives a constriction member 329, such as a cinchable teflon or teflon-coated loop or cable. The recess or groove can extend along the length of the support body 325.

In some embodiments, the support body 325 can include multiple holes or apertures 327, 328. The support body depicted in FIGS. 3 and 3A is generally flat, providing a low profile that can efficiently be advanced under the left atrial appendage. As shown in FIG. 3, the support body can be configured in a "U" or horseshoe shape. Similarly, a cross-section of the support body 325 can provide a "U" or horseshoe shape. As depicted in FIG. 3A, support frame 326 or nitinol wire can extend along an outer or peripheral portion of the support body 325, and the holes 327, 328 can be positioned toward the interior of the support body. In use, a suture thread can be placed peripheral to the holes, inside of a groove provided by the support body 325. Rivets (not shown here), which may be manufactured from silicone, can be placed in the holes (e.g. extending between a hole in a top section of the support body and a corresponding hole in a bottom section of the support body), thereby holding or retaining the suture thread in place within the support body groove. In some cases, the rivets can be configured in a barbell shape, so that enlarged opposing ends of the rivets extend through the corresponding opposed holes of the support body (e.g. with head of rivet sitting outside the top and bottom surfaces of the support body).

In some instances, two threads can be placed in the support body groove, and can be threaded around every other rivet in an alternating fashion, so that when the surgeon or operator pulls on one suture thread, it cuts through a first set of rivets as it exits the support body and is delivered to the target tissue. Similarly, the surgeon can pull on the other suture thread, which cuts through a second set of rivets as it exits the support body and is delivered to the target tissue. In some cases, the rivets can be glued in place to the support body, so that when the central portion of the rivet is severed, the end portion or head remains attached to the support body, and rivet pieces are not ejected at the treatment site within the patient. In this way, rivets can be used to hold the suture in place, prior to deployment. And during delivery, the suture thread can be unzipped out of the support body. Relatedly, two suture threads can be loaded onto the support body, and one suture thread can remain in place while the other suture thread is pulled out. Each suture thread can be held in place with its own respective set of rivets, and pulling on one suture can operate to rip the rivets that are specific for that suture.

Generally, FIGS. 3 and 3A depict a fixed head configuration for a ligature delivery system 300. Such a configuration may include one axis of rotation, or none at all. In use, the support frame 326 can bend relative to the distal head 324, as the hoop assembly is deflected by anatomical features as the delivery systems is moved within the patient's body. The distal head 324 may include slots or recesses 323, so as to receive the base of the support frame 326 as the support frame bends forward and backward relative to the distal head 324. In this way, the slot 323 can distribute the bend of the support frame 326, so that the base of the support frame bends with a larger radius of curvature (i.e. as compared to a bend in the base when the slot is not present). Hence, it is possible to achieve a greater degree of amount of bending in the support frame 326, with a lower amount of stress. In operation, the flexible hoop assembly 321 can flex significantly (e.g. 180 degrees) without snagging on anatomical features of the patient. In some cases, the flexible hoop assembly 321 can bend so that it is generally aligned with the support frame or elongate shaft of the device. For example, a nitinol spine or support frame 326 can be flexible, such that the hoop assembly and constriction member flex in response to contact with firm anatomical features. However, the nitinol spine or support frame 326 can also operate to apply a downward force or other force toward the base of the left atrial appendage, when advancing the hoop assembly 321 over the appendage. According to some embodiments, two or more components of the hoop assembly 321 (e.g. support body 325 and constriction member 329) can be disposed in approximately the same plane, and the co-planar relation can be maintained by a temporary or elastic connection between the components.

When using a fixed head configuration with no rotatable joints, such as that shown in FIGS. 3 and 3A, the surgeon or operator can rotate the device by turning a handle which is in fixed relationship with the distal head 324. In some cases, the cable or constriction member 329 can fit within an edge or groove of the support body 325. During use, the cable 329 can move along with the support body 325. When cinched down, the cable 329 can be pulled out of a groove or recess of the support body 325. In some instances, it may be desirable to retain alignment between the cable 329 and the support body 325. For example, the ligature delivery system can be provide with a structure that keeps the cable 329 and the support body 325 in the same plane during use. Hence, the cable 329 and the support body 325 can remain in positional relationship with one another as the system is maneuvered throughout the patient anatomy (e.g. advancing/retracting through thorax, between ribs, and the like).

The cable 329 and support body 325 may not be direction coupled with one another, although they can bend readily along with one another.

FIG. 4 depicts aspects of an exemplary ligature delivery system 400 according to embodiments of the present invention. As shown here, the system 400 includes a proximal section 402 and a distal section 404. The distal section 404 includes a pivotable hoop assembly 422 configured to deliver one or more suture threads to an anatomical feature of a patient, such as the left atrial appendage.

As depicted in FIG. 4, a system 400 can include one or more sliders or ligature control mechanisms 410, 420. As shown here, sliders 410, 420 are in a forward or distal position. This can represent a starting or initial configuration for the system, where the ligatures are held by the support body of the hoop assembly. The sliders or ligature control mechanisms can be moved in a proximal direction, as indicated by arrow A, so as to deliver the respective sutures to a desired anatomical feature, such as the left atrial appendage. For example, slider 420 can be actuated to deliver a first suture, and thereafter or concurrently, slider 410 can be actuated to deliver a second suture. System 400 can also include a constriction member control mechanism having a knob 470 and a trigger 480. In use, the operator can pull the knob 470 proximally and tighten the constriction member. Relatedly, the operator can pull the trigger 480 proximally and loosen the constriction member. In some cases, the system 400 may include a ratchet mechanism (not shown) which allows for incremental tightening of the constriction member. Actuation of the trigger can operate to release the ratchet mechanism (e.g. in association with a spring loaded mechanism that releases the constriction cable to an open position). In some cases, system 400 may include a safety lock mechanism 490, which can operate to lock the trigger 480 and thus prevent the trigger from being activated (i.e. such that the constriction member is loosened) until such a time as loosening of the constriction member is desired. When the operator wishes to loosen the constriction member, the operator can disable the safety lock mechanism 490 and proceed with actuating the trigger 480 so as to loosen the constriction member.

Figure 4A:
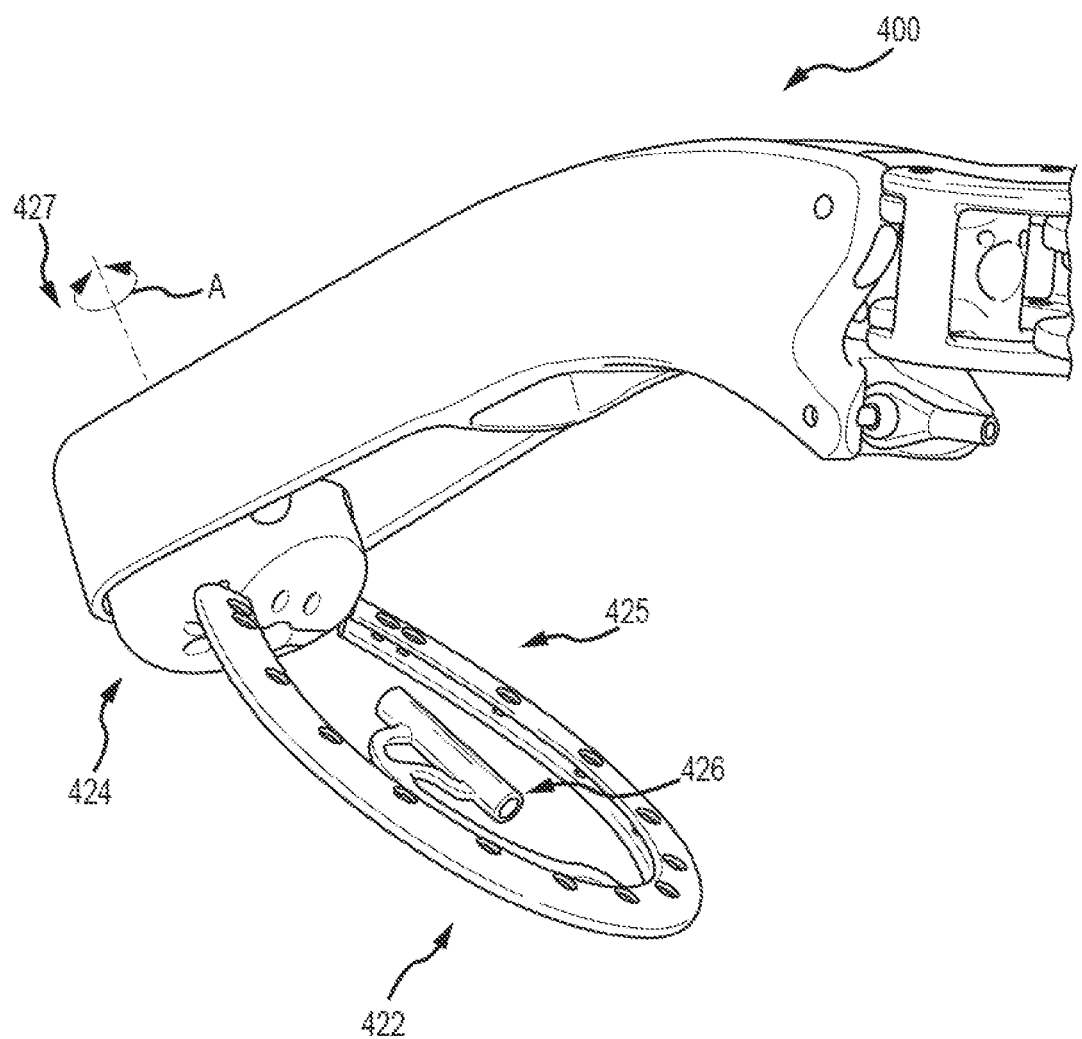
FIGS. 4A, 4B, and 4C depict aspects of ligature delivery systems according to embodiments of the present invention.

FIG. 4A shows a magnified view of hoop assembly 422. As depicted here, the hoop assembly includes a support body 425, which is coupled with a deflector body 424, for example via a support frame (as described elsewhere herein). Deflector body 424 can be pivotally coupled with a distal head 427 of the system 400. The support body 425 includes a containment structure 426 such as a tube.

Figure 4B:
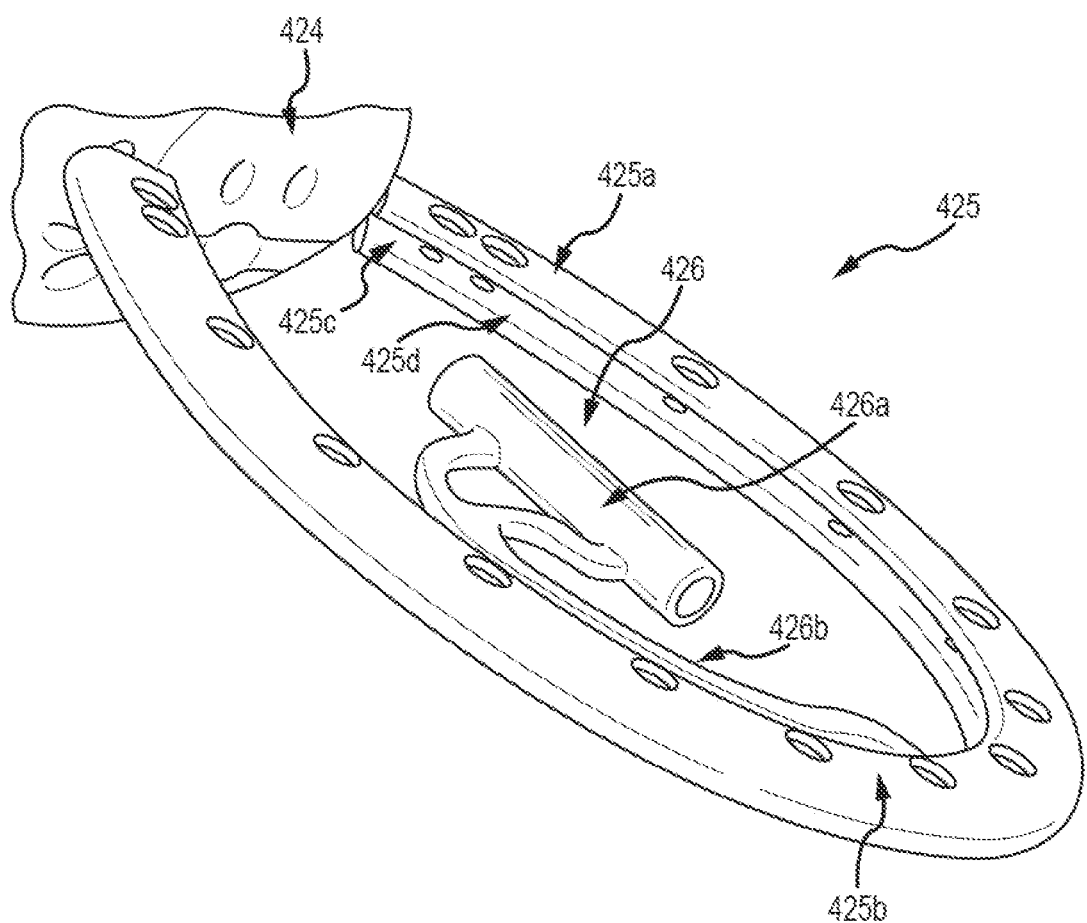

FIG. 4B depicts a further magnified view of support body 425 and containment structure 426. The containment structure 426 includes a tube 426a coupled with an upper edge 425a of the support body (e.g. at an apex 425b of the support body) via an attachment structure 426b. The containment structure 426 can be used to help guide the sutures, when the sutures are deployed, to the target tissue. Relatedly, the containment structure 426 can operate to keep the sutures below the a constriction member (e.g. Teflon coated cable), so that the sutures do not trap the cable against the patient tissue when the sutures are deployed. For example, the constriction member (not shown) can exit the deflector body 424 and travels through the tube or guide 426a, and follows the path of the support body 425. The attachment structure 426b can be constructed using a very soft and flexible material, such as silicone or urethane. Hence, when the cable or constriction member is held by the guide 426a, the guide 426a can be positioned in alignment with the support body 425 (e.g. in contrast to the central positioning of guide 426a shown here). Hence, the guide 426a can conform with the positioning of the constriction member, and when the constriction member is on or aligned with the support body, the guide 426a is as well.

In use, the constriction member can be tightened down to a smaller diameter (e.g. smaller than the diameter of the support body), the guide 426a can follow the constriction member (e.g. by moving toward the deflector body 424). In this way, the guide 426a, in combination with the attachment structure 426b, can operate to keep sutures, which may be positioned along a groove 425c of the support body (e.g. between upper edge 425a and lower edge 425d of the support body), positioned below the constriction member. As the constriction member is constricted, the guide 426a can eventually approach or contact the patient tissue, such as the left atrial appendage. Hence, an upper barrier is presented above the sutures, the barrier extending from the apex 425b of the support body to the patient tissue, and the sutures can be deployed out of the groove 425c and onto the patient tissue. As the sutures are tightened, they remain below the guide 426a and attachment structure 426b (e.g. between the tissue and the containment structure). This prevents the sutures from traveling to a position that is above the constriction member (e.g. such that the containment structure would be between the sutures and the patient target tissue).

Accordingly, this flexible connection between the constriction member and the support body can provide a guide for the sutures when the constriction member is contracted. That is, the sutures are guided as they contract to stay below the cable constriction member so as to not trap the constriction member or other device elements against the patient tissue.

Although not shown in FIG. 4B, the hoop assembly can include a flexible support frame or spine (such as a nitinol wire) that supports the support body 425. In this way, the support body 425 can flex up and down. The hoop assembly can also be controllably rotatable about a vertical axis, as depicted in FIG. 4A, for positioning under the anatomic structure (e.g. left atrial appendage).

Figure 4C:
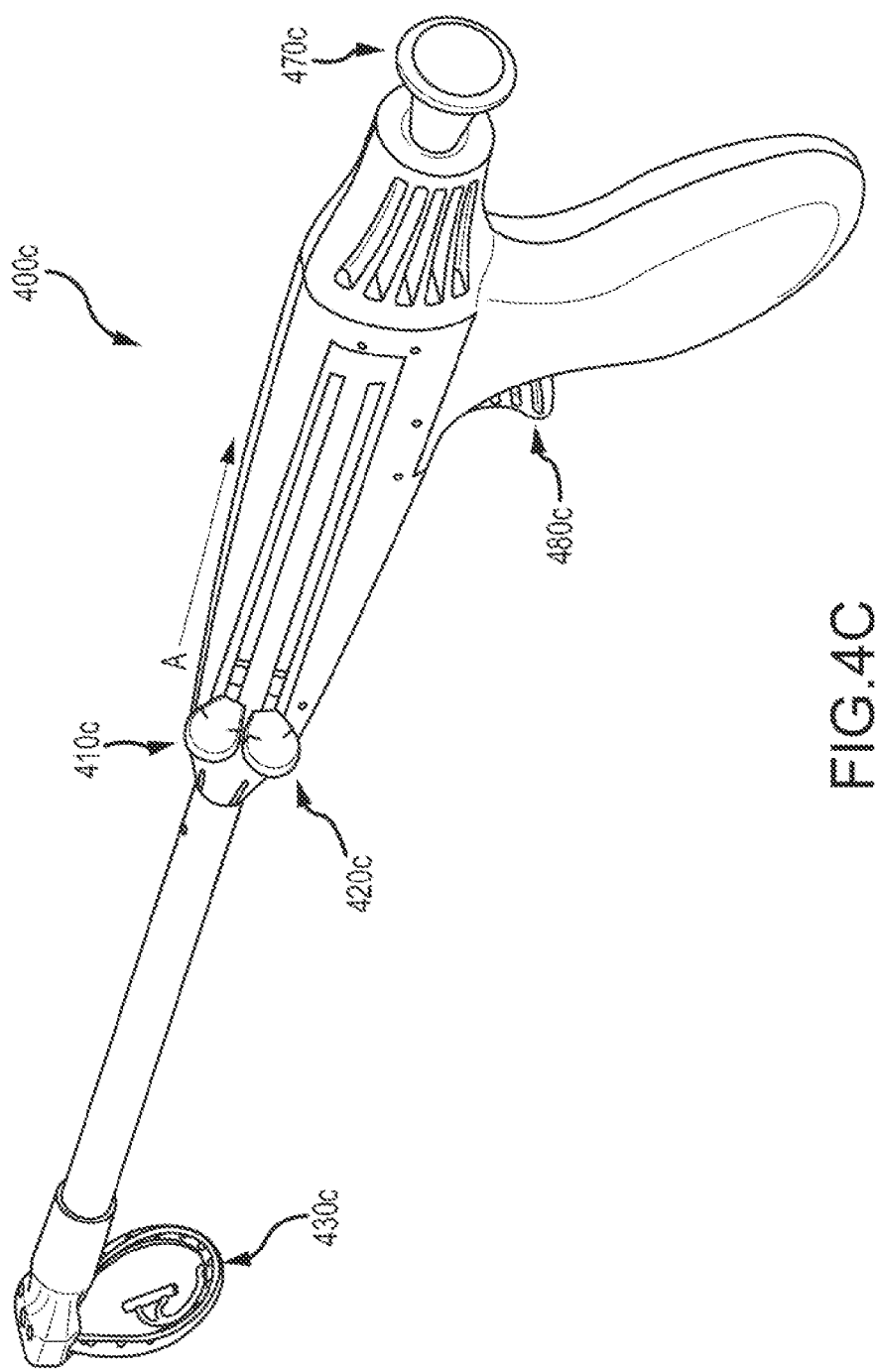

As shown in FIG. 4C, a ligature delivery system 400c can be provided in a fixed head configuration. In some case, as depicted in FIG. 4, a ligature delivery system can be provided as a single axis rotatable head configuration. In some cases, a deflector body 424 can rotate about an axis A as indicated in FIG. 4A. A linkage assembly 428 can also allow a distal head 427 of the system to pivot side to side (yaw), as indicated in FIG. 4. For example, the distal head 427 can pivot about a vertical axis at joint or linkage assembly 428. As shown here, system 400 includes a rotating disk or yaw control 430, whereby the user or operator can effectuate yaw in the hoop assembly 422 by rotating the disk or yaw control 430. The linkage assembly 428 can also allow the distal head to pivot up and down (pitch). As shown here, system 400 includes a lever or pitch control 450, whereby the user or operator can effectuate pitch in the hoop assembly 422 by actuating the lever 450. In some configurations, actuation of the lever 450 can also or alternatively operate to effectuate side to side motion at joint or linkage assembly 428. According to some embodiments, the system 400 can include a trigger release 455 in operative association with the lever 450, such that the lever 450 can be locked in a desired position, thus locking the orientation of the hoop assembly in a desired configuration. The curvature or configuration of the distal section 404 in FIG. 4 is well suited for use in a right side or subxyphoid approach. The linkage assembly 428 can accommodate the presence and operation or actuation of multiple elements (e.g. push rods, constriction cable, sutures, and so on) as the distal head is maneuvered about in pitch and yaw movements. Further, the surgeon or operator can rotate the entire system 400 by turning or rotating the handle 401.

In contrast to the configuration depicted in FIG. 1, where the deflector body 142 has two degrees of freedom provided by axis 144 and axis 146, the configuration depicted FIG. 4A has one degree of freedom provided by axis A. The angle presented by the hoop assembly in FIGS. 4A and 4C allow the hoop assembly to be advanced under the left atrial appendage, without having a pitch pivot associated with the device. The hoop assembly can also be sufficiently flexible (e.g. in the configurations of FIGS. 4A and 4C), such that the device can be withdrawn from the patient body without actively tucking the hoop assembly up against the elongate shaft or support mechanism of the system.

As depicted in FIG. 4C, a system 400c can include one or more sliders or ligature control mechanisms 410c, 420c. As shown here, sliders 410c, 420c are in a forward or distal position. This can represent a starting or initial configuration for the system, where the ligatures are held by the support body of the hoop assembly. The sliders or ligature control mechanisms can be moved in a proximal direction, as indicated by arrow A, so as to deliver the respective sutures to a desired anatomical feature, such as the left atrial appendage. For example, slider 420c can be actuated to deliver a first suture, and thereafter or concurrently, slider 410c can be actuated to deliver a second suture. System 400c can also include a constriction member control mechanism having a knob 470c and a trigger 480c. In use, the operator can pull the knob 470c proximally and tighten the constriction member 430c. Relatedly, the operator can pull the trigger 480c proximally and loosen the constriction member. In some cases, the system 400c may include a ratchet mechanism (not shown) which allows for incremental tightening of the constriction member. Actuation of the trigger can operate to release the ratchet mechanism (e.g. in association with a spring loaded mechanism that releases the constriction cable to an open position).

Figure 5:
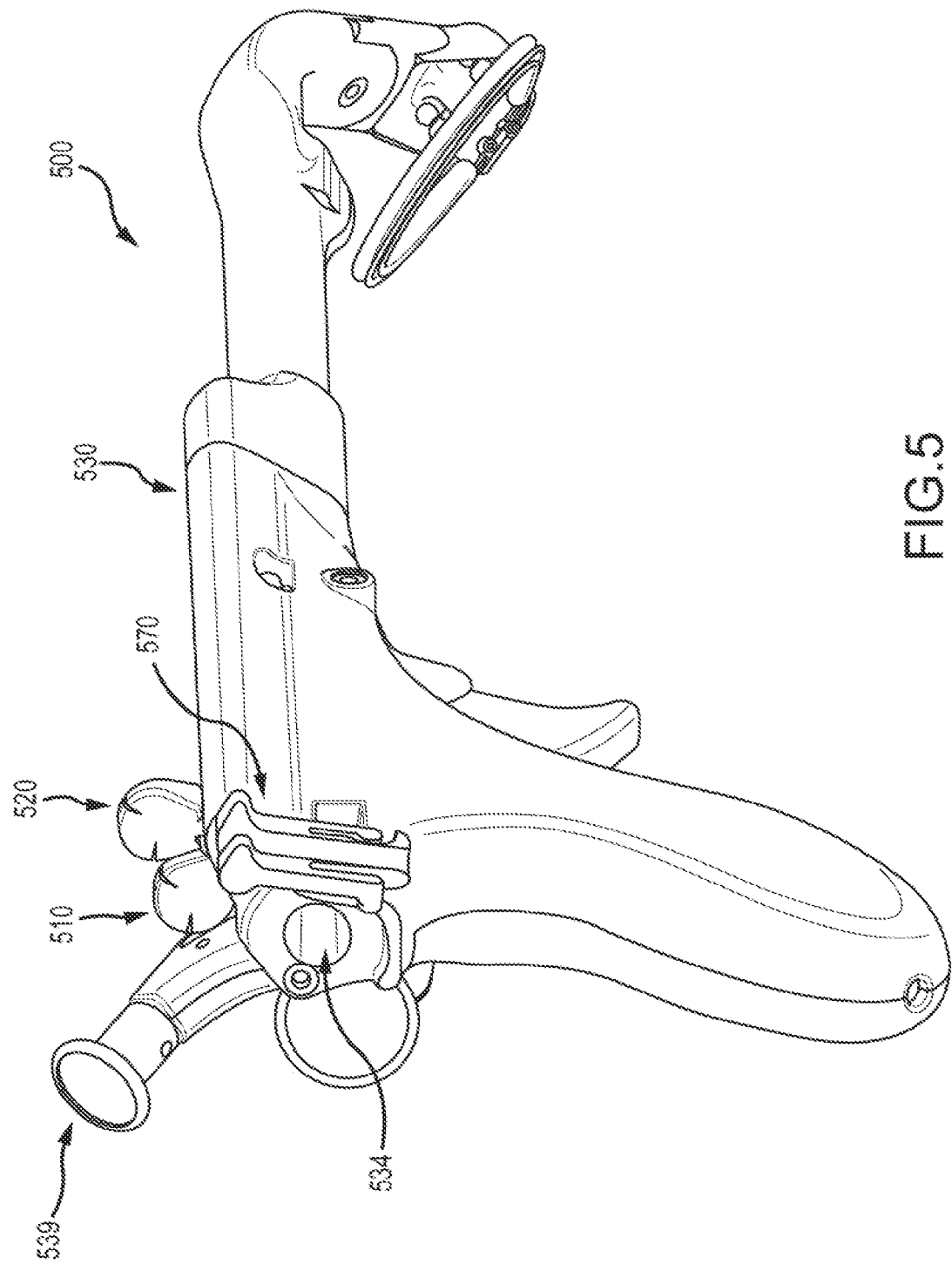
FIG. 5 depicts aspects of a ligature delivery system according to embodiments of the present invention.

FIG. 5 depicts a ligature delivery system 500 having sliders or suture control mechanisms 510 and 520 that operate as a suture engagement assembly, and can be used when delivering sutures to patient tissue. For example, when loading sutures onto the delivery system, a surgeon, operator, or other individual can position a suture loop about the support body, so that the suture loop is placed within a groove of the support body. A knot of the suture can be placed in a pocket (e.g. of the deflector body), and the proximal tail or thread of the suture can be pulled proximally, so as to remove excess suture or slack that may be remaining in the suture loop. The proximal tail or thread of the suture can be attached with a suture control mechanism (e.g. 510 or 520). In use, the suture control mechanism can be actuated (e.g. drawn proximally) so as to cinch down or contract the distal loop of the suture. Hence, a support mechanism 530 of the system may include an engagement assembly that receives one or more ligature assemblies. The system 500 may also include a knob or cable cinch control mechanism 539 in operative association with the constriction member. Hence, the user can pull the cinch control mechanism 539 in a proximal direction so as to tighten or constrict the constriction member. Relatedly, the user can actuate a trigger or release mechanism (e.g. as depicted in FIG. 4C), so as to loosen the constriction member. Optionally, in some configurations, the user can push the knob in a distal direction so as to loosen the constriction member.

According to some embodiments, the system or support mechanism 530 may include a port or lumen 534 that is adapted to receive a visualization mechanism such as an endoscope. According to some embodiments, a delivery system 500 may include a lever assembly 570. In use, the operator or surgeon can place rubber bands or other fixation devices about the levers and scope, so as to keep the scope advanced in a distal direction, and to prevent the scope from moving in a proximal direction. In some cases, the rubber band or fixation device can operate to hold the scope in a distal position, for example pressed distally against a stop as discussed elsewhere herein. In this way, the lever assembly 570 can help to keep the scope oriented in a desired position. In some cases, the lever assembly 570 in combination with the fixation devices can help to keep the scope from rotating within the lumen or passage 534.

Figure 6:
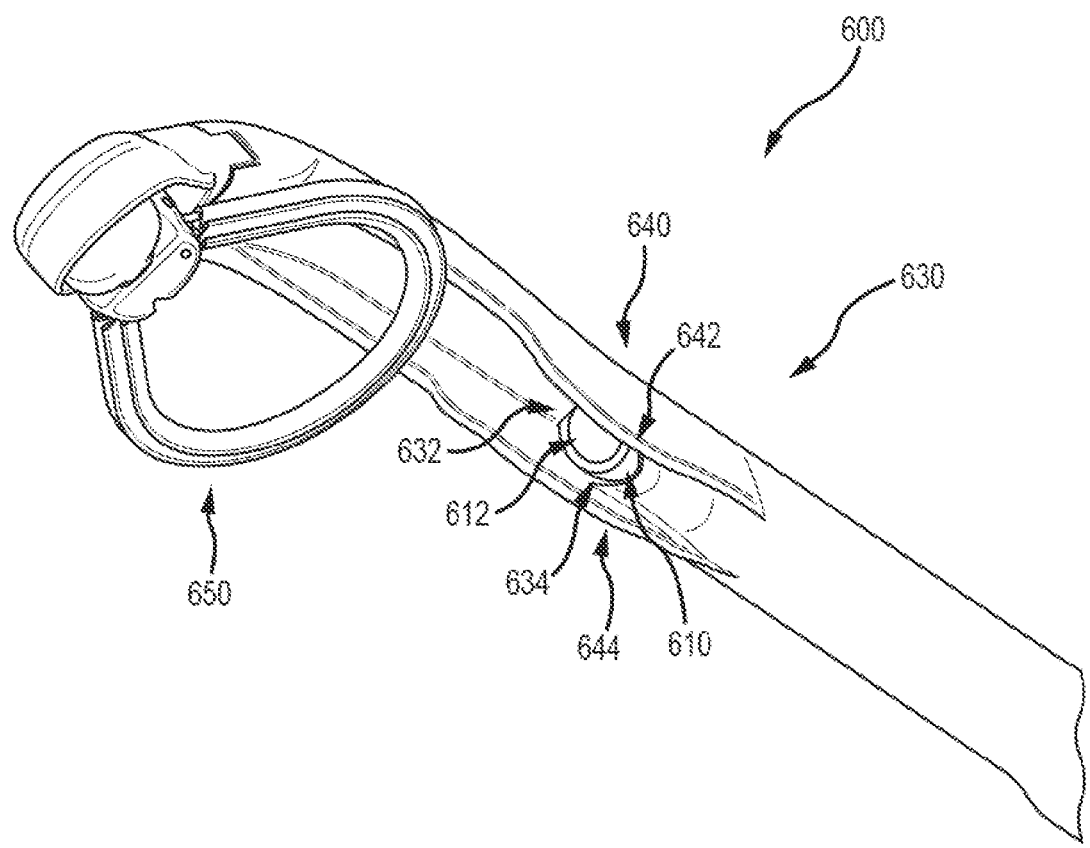
FIG. 6 depicts aspects of a ligature delivery system according to embodiments of the present invention.
Figure 6A:
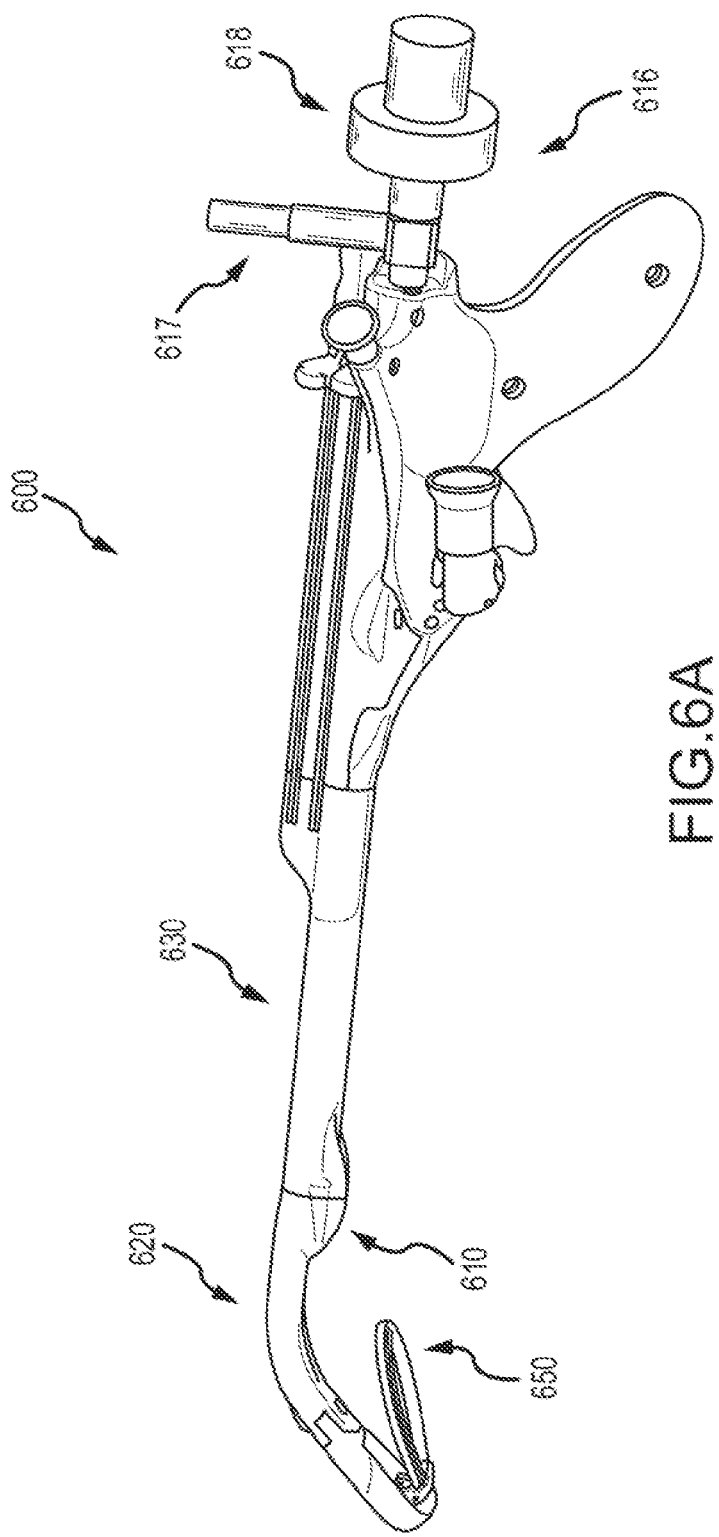
FIGS. 6A and 6B depict aspects of ligature delivery systems according to embodiments of the present invention.

FIG. 6 depicts a ligature delivery system 600 having a visualization mechanism 610, such as a scope. As shown here, the visualization mechanism 610 is positioned at a cut-out or recessed location, which can help the operator or surgeon to visualize actuation and placement of the hoop assembly. The visualization mechanism 610 can be positioned within a lumen of a support mechanism or elongate shaft 630 of the system. As depicted in FIG. 6A, the visualization mechanism 610 can be positioned proximal to a bend 620 in the support mechanism 630. As depicted in the cut-away cross-section view of FIG. 6B, the visualization mechanism 610 can be oriented at an angle (e.g. 30 degree angle) so that optical elements of the visualization mechanism face toward the hoop assembly.

In use, the visualization mechanism 610, which may be provided as a scope such as an endoscope, can be inserted into and advanced distally within the support mechanism 630. With returning reference to FIG. 6, the support mechanism 630 includes a stop 632 which operates to keep the visualization mechanism 610 from extending out from the lumen or passage 634 within which it is placed. Hence, a surgeon or operator can insert a scope mechanism into the proximal portion of the delivery system 600, and advance the scope distally until a distal portion of the scope mechanism contacts the stop 632. In some cases, a delivery system 600 may include a locking mechanism that operates to lock the visualization mechanism 610 in place, so as to prevent or inhibit the visualization mechanism from rotating within or relative to the support mechanism 630. As shown here, support mechanism 630 includes an offset mechanism 640, which can include two wings or flaps 642, 644 extending from the body of the support mechanism.

The lens 612 of the visualization member can be positioned between the flaps 642, 644, such that the flaps help to keep tissue away from the lens surface. In this way, the lens 612 can remain clear of fluid, debris, and other material which may compromise the image obtained by the visualization member. For example, fogging, moisture, and blood and other body fluids can impair the imaging ability of the visualization member when present on the lens. As discussed elsewhere here, the visualization mechanism 610 can be constructed so that the lens 612 is oriented at a desired angle, relative to the scope body, support mechanism, and/or hoop assembly. In this way, in use, when the hoop assembly is deployed or guided toward the anatomical feature (e.g. left atrial appendage), the user can visualize the anatomical feature and the hoop assembly concurrently. For example, when the hoop assembly is deployed or rotated toward the left atrial appendage, the field of view as presented to the operator or surgeon includes the left atrial appendage, and the left atrial appendage is surrounded or encompassed by the hoop assembly. The operator or surgeon can maneuver the system 600 so that the hoop assembly is placed over the distal portion of tip of the left atrial appendage, and accordingly the image presented to the operator or surgeon is similar to a bulls-eye or target, wherein the left atrial appendage is at the central portion of the image and the hoop assembly is at the periphery. The lens and/or other optical components of the visualization mechanism can provide the user with a sufficiently wide field of view, such that the user can view the hoop assembly as it moves back and forth, or up and down, or in various directions throughout a range of motion. For example, the scope view is wide enough so that lateral movement or yaw of the hoop assembly throughout a range of motion can be seen by the operator. In some cases, the operator can view the top and bottom surfaces of the hoop assembly as the hoop assembly pitches throughout a range of motion. In some case, the operator can view the outer edge or periphery of the hoop assembly.

Because the visualization mechanism 610 is attached with the support mechanism 630, the field of view provided by the lens 612 moves within the patient as the surgeon or operator moves the support mechanism. In some cases, visualization mechanism 610 can be external to the support mechanism 630. In some cases, visualization mechanism 610 can be unattached with or independent of the support mechanism 630. For example, in some instances, the support mechanism can be inserted through a first access point into the body of the patient, and the visualization mechanism can be inserted into a second access point into the body of the patient. Hence, the surgeon or operator may keep the visualization mechanism stationary with respect to the support mechanism. Relatedly, the surgeon or operator may maneuver the visualization mechanism independently of the support mechanism, and the surgeon or operator may maneuver the support mechanism independently of the visualization mechanism. Hence, in use, anatomical features such as body tissue can appear to remain stationary within the field of view (e.g. where the scope is not coupled with the support mechanism), or the anatomical features can appear to move within the field of view (e.g. where the scope is disposed within the support mechanism).

As shown in FIG. 6A, a distal portion 616 of a visualization mechanism 610 can extend proximally from the support mechanism 630 of the delivery system 600. In some cases, a visualization mechanism may include or operate in association with a light source 617. In some cases, a visualization mechanism may include a coupling mechanism 618 for attaching with a camera or other recording device.

Figure 6B:
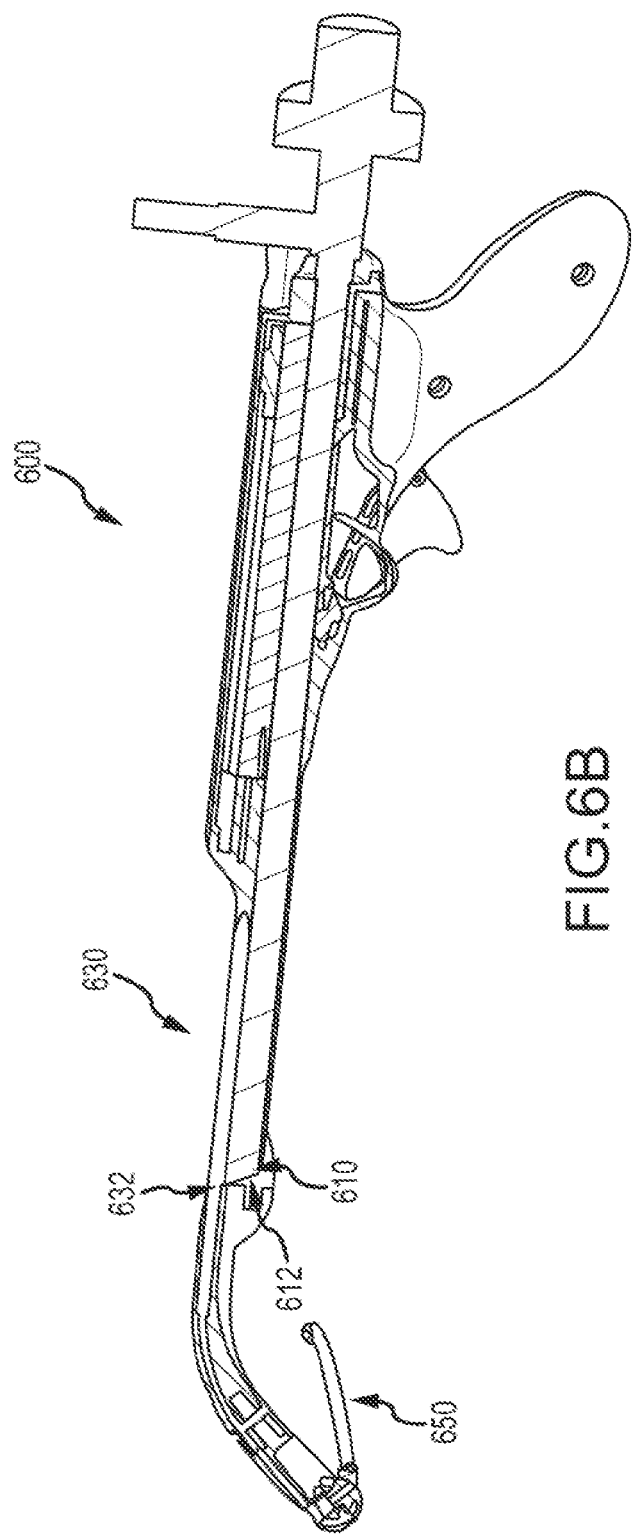

In the cut-away view of FIG. 6B, it can be seen that stop 632 operates to keep the visualization mechanism 610 from extending distally from the support mechanism 630. As shown here, the lens 612 affords the user or operator with a field of view that includes the hoop assembly. Hence, by providing a scope or visualization mechanism 610 that is offset from the distal end of the system, and by providing a hoop assembly 650 in a trailing configuration, such that the hoop assembly is disposed distal to the visualization member or lens 612, the user can view the operation of the hoop assembly at the site of treatment (e.g. at the left atrial appendage), while having a distally oriented field of view that is aligned generally with the support mechanism or body of the delivery system, and the lens does not contact the patient tissue because of the protective action of the wings. In some cases, the visualization mechanism or scope is about 30 cm long and about 10 mm in diameter. In some cases, the lens is offset from the body of the scope at an angle of about 30 degrees. The support mechanism 630 can be configured to accept or receive any of a variety of scope sizes and shapes. In some cases, a surgeon or operator can use multiple scopes within the context of a single surgery, by removing one scope from the support mechanism and replacing it with a different scope.

Figure 7:
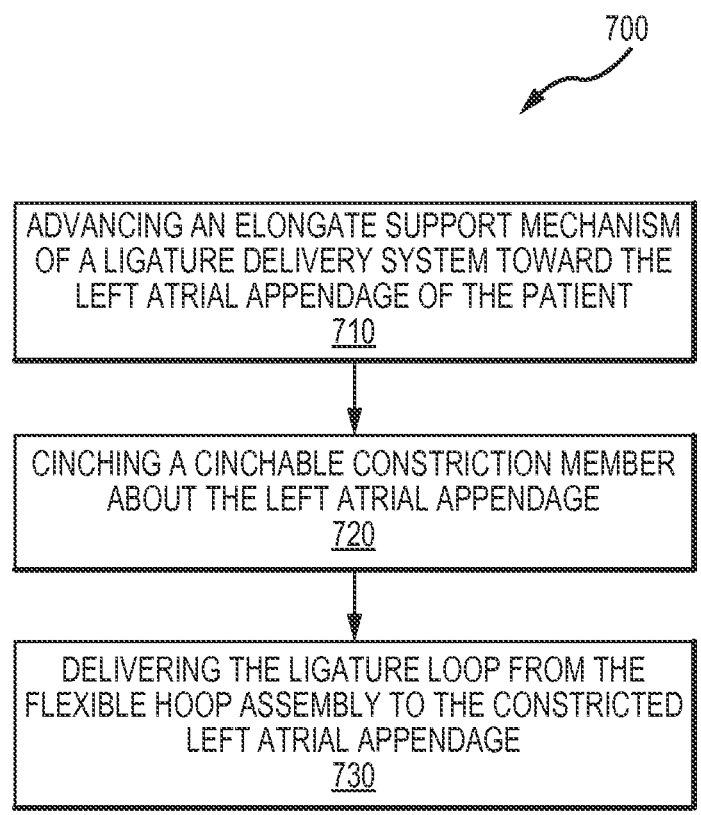
FIG. 7 depicts aspects of a ligature delivery method according to embodiments of the present invention.

FIG. 7 depicts aspects of a ligature delivery method 700 according to embodiments of the present invention. As shown here, a method of delivering a ligature loop to a left atrial appendage of a patient can include advancing an elongate support mechanism of a ligature delivery system toward the left atrial appendage of the patient, as indicated by step 710. In some cases, the ligature delivery system includes a flexible hoop assembly coupled with the distal portion of the elongate support mechanism, and the flexible hoop assembly is disposed in a trailing configuration. Further, methods may include cinching a cinchable constriction member about the left atrial appendage, as indicated by step 720, so as to constrict the left atrial appendage. Still further, methods may include delivering the ligature loop from the flexible hoop assembly to the constricted left atrial appendage, as indicated by step 730.

All patent filings (including patents, patent applications, and patent publications), scientific journals, books, treatises, technical references, and other publications and materials discussed in this application are incorporated herein by reference in their entirety for all purposes.

Ligature Assemblies

Figure 8:
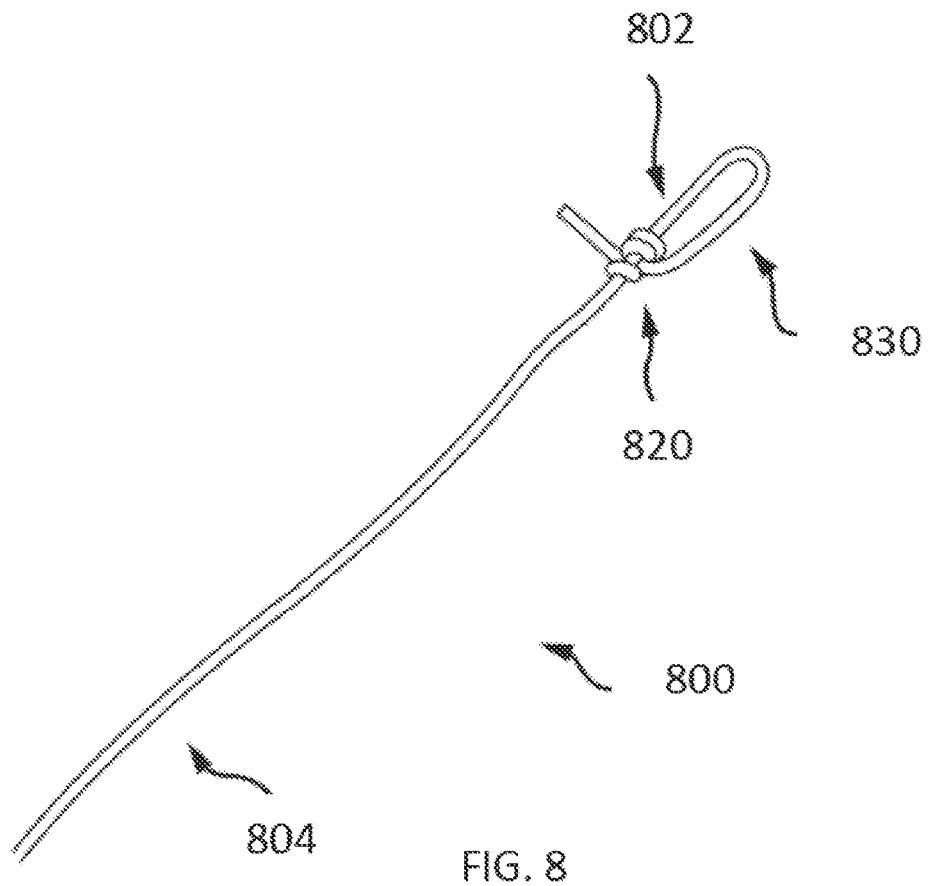
FIG. 8 depicts aspects of a ligature assembly according to embodiments of the present invention.

FIG. 8 illustrates aspects of an exemplary ligature assembly 800 according to embodiments of the present invention. In some cases, a ligature assembly may be referred to as a ligating loop or a surgical snare. As depicted here, the ligature assembly 800 includes a ligature thread or closure means or mechanism. In some instances, a ligature assembly can be provided as a left atrial appendage ligature assembly. The ligature assembly or thread 800 can be pre-formed or pre-tied in such a way so as to present a knot 820 and a loop portion 830. Generally, the knot 820 is disposed toward a distal portion 802 of the ligature thread 800. In use, the proximal tail portion 804 can be pulled, thus tightening or cinching the ligature loop portion 830.

According to some embodiments, the knot 820 is provided as a slip knot, sliding knot, running knot, or the like. For example, as the user or operator pulls the proximal thread tail 804, the knot 820 can allow a portion of the thread sliding therethrough to move lengthwise freely in one direction of pull (e.g. proximally). In this way, the knot 820 can perform as a non-return knot. A knot 820 may be provided as a simple knot or a complex knot. Suitable knot configurations may also include laparoscopic knots, endoscopic knots, intracorporal knots, extracorporeal knots, intraabdominal knots, surgical knots, and the like. In some instances, a ligature assembly may include a knotted thread or suture having a distal loop portion and a proximal tail portion. As further discussed elsewhere herein, the ligature delivery systems and methods provided in the instant disclosure allow a surgeon or operator to constrict the loop portion 830 about the patient's anatomy without having the thread cut into or form a groove in the patient's tissue.

As discussed elsewhere herein, a ligature delivery system may include a pocket or stop that receives the ligature assembly knot 820. In some instances, the pocket or stop may include a slotted shelf or two protrusions which operate to prevent proximal translation of the knot relative to the support mechanism or deflector mechanism when the proximal tail portion 804 of the ligature assembly is drawn proximally. In use, the surgeon or operator can use the ligature delivery assembly to place the ligature thread loop 830 about the anatomical structure, and can draw the thread tail 804 proximally, so as to cinch the thread loop relative to the patient anatomical structure. Accordingly, the yoke or stop can be used to provide an opposing force when drawing a translating portion of the ligature thread proximally through the knot 820, so as to cinch or reduce the diameter of the ligature loop. In this way, the knot can be restrained by the pocket. The translating portion of the thread passes through the knot 820. In this way, the loop thread can be cinched by applying counter fraction via the pocket. A sliding knot can operate to secure itself when tightened. Once tightened in place relative to the anatomical structure, the suture thread loop or closure means can be unloaded from the ligature delivery system, thus also releasing the knot from the pocket. Thereafter, the suture loop or closure means remains in place about the anatomical structure (e.g. by virtue of the knotted loop). The proximal tail portion 804 can be released from the ligature delivery system, and the ligature delivery system can be removed or retracted away from the patient, leaving the suture thread fixed to the patient anatomy. The surgeon or operator can then clip the excess proximal tail portion of the suture thread. In this way, the closure means or ligature loop can be used to tie off the left atrial appendage of a patient, the cecal appendix, or any other desired structure within a patient.

Figure 9:
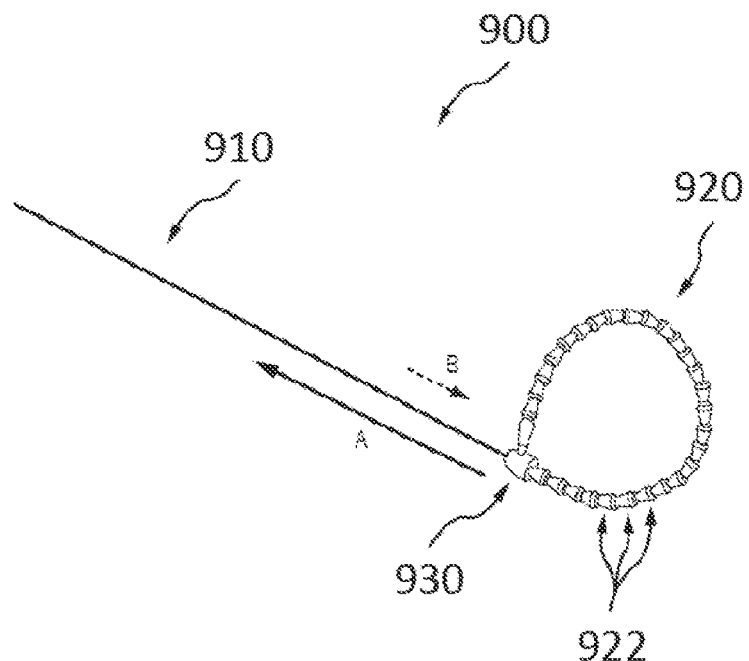
FIG. 9 depicts aspects of a ligature assembly according to embodiments of the present invention.

FIG. 9 illustrates another exemplary ligature assembly or snare 900 according to embodiments of the present invention. As shown here, the ligature assembly includes a proximal tail portion 910 and a distal portion 920 which can be formed into a loop, for example by passing the proximal portion through a ratchet mechanism 930. In this way, the distal portion can provide a ligature loop or closure means. The distal portion includes a series of projections 922 which may include teeth, barbs, beads, or the like. Typically, the projections are shaped so that they can be easily pulled through the ratchet mechanism 930 in one direction as indicated by arrow A, and resist movement through the ratchet mechanism 930 in the opposing direction as indicated by arrow B. For example, the projection may be triangular in shape or have a sloped surface. In this way, the coordinated operation between the projections 922 and the ratchet mechanism 930 operate in a manner similar to that of a one-way or non-return knot. In some instances, the ratchet mechanism 930 may include a flexible pawl deforms when rigid projections are passed along the ratchet. In some cases, the projections are flexible and deform when passed along a rigid pawl of the ratchet. Once the projection proceeds past the ratchet or pawl (in the direction indicated by arrow A), it is prevented or inhibited from returning in the opposite manner (as indicated by arrow B). In this way, the loop or closure mechanism can be cinched or constricted as desired to a particular diameter or size, and when the projection is locked against the ratchet or pawl the loop cannot be expanded or uncinched.

In some cases, a ligature assembly includes a threadlike suture that can reside partially within a tube or carrier. In some case, the suture is pre-formed with a knot. Hence, when a looped distal end of the ligature is positioned at a desired location about the LAA, the proximal portion of the ligature can be pulled or actuated, so as to tighten the loop, thus securing the knot. Some ligature assemblies may include a suture which extends from a distal end of the carrier in the form of a loop, having a sliding knot which secures itself when tightened. In some cases, ligature assemblies include a suture that is non-absorbable by the patient's body. Embodiments of the present invention encompass systems and methods for use in conjunction with such ligature assemblies, for the delivery of a suture to the patient's LAA.

The thread or suture can include plain gut elements, synthetic polymers or copolymers, polymeric filaments, monofilament, polyester or other suitable materials, coated configurations, braided configurations or threads, and the like. In some instances, the diameter of the ligature thread may be between about 15 and 20 thousandths of an inch. In some instances, other thread diameters may be used. It is understood that the ligature delivery system may include thread guides, slots, grooves, and the like, which are sized or configured to operate with any ligature thread diameter, cross-section, or configuration. Similarly, the ligature delivery system may include knot or ratchet guides, pockets, stops, and the like, which are sized or configured to operate with any ligature thread knot or ratchet size or configuration.

In some embodiment, the ligature assembly or closure means may include an elastic or stretchable band or ligature loop that does not include a knot, ratchet, or proximal tail. Such a closure means or mechanism can be wrapped in a generally circumferential manner about the hoop assembly of the ligature delivery system.

All patent filings (including patents, patent applications, and patent publications), scientific journals, books, treatises, technical references, and other publications and materials discussed in this application are incorporated herein by reference in their entirety for all purposes.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While exemplary embodiments have been described in some detail, by way of example and for clarity of understanding, those of skill in the art will recognize that a variety of modification, adaptations, and changes may be employed. Hence, the scope of the present invention should be limited solely by the claims.

We claim:

1. A ligature delivery system for applying a left atrial appendage ligature on a left atrial appendage, the ligature delivery system comprising:
   an elongate support shaft having a proximal portion and a distal portion;
   a handle portion located at the proximal portion of the elongate support shaft;
   a flexible hoop assembly coupled with the distal portion of the elongate support shaft, the flexible hoop assembly defining a support body and a support frame, wherein the support body comprises a lumen configured to receive the support frame within; and
   one or more constriction members coupled to the flexible hoop assembly, wherein the support body is configured to support the one or more constriction members, wherein the one or more constriction members are guided via a plurality of flaps of the support body, wherein the plurality of flaps define a plurality of channels in which the one or more constriction members are received; and a deflector body configured to pivot in two axes relative to the elongate support shaft, wherein the support frame of the flexible hoop assembly is coupled with the distal portion of the elongate support shaft via the deflector body, wherein the deflector body comprises a plurality of pockets configured to hold the one or more constriction members guided from the plurality of flaps.

2. The ligature delivery system according to claim 1, further comprising a constriction control member operatively linked to the constriction member such that actuation of the constriction control member cinches the constriction member about the left atrial appendage.

3. The ligature delivery system according to claim 1, further comprising a ligature control member located on the handle portion, the ligature control member configured to reduce a diameter of the left atrial appendage ligature to cinch the left atrial appendage ligature about the left atrial appendage.

4. The ligature delivery system according to claim 1, further comprising a deflection control member located on the handle portion and linked to the deflector body, such that actuation of the deflection control member causes the deflector body to pivot relative to the elongate support shaft.

5. The ligature delivery system according to claim 1, wherein the constriction member is configured to be removed from the flexible hoop assembly when an inner surface of the support body is exposed.

6. The ligature delivery system according to claim 5, wherein the support frame is biased to hold the support body in a trailing configuration whereby a free portion of the support body is disposed proximal to the distal portion of the elongate support shaft.

7. The ligature delivery system according to claim 6, wherein the constriction member comprises an undeployed configuration and a deployed configuration, wherein in the deployed configuration the constriction member is configured to be cinched to constrict in diameter about the left atrial appendage.

8. A method of delivering a ligature loop to a left atrial appendage of a patient, the method comprising:

advancing an elongate support shaft of a ligature delivery system toward the left atrial appendage of the patient, wherein the ligature delivery system includes a flexible hoop assembly coupled with a distal portion of the elongate support shaft, the flexible hoop assembly defining a support body, being disposed in a trailing configuration, and being adjustable about two axes via a deflector body such that the flexible hoop assembly can pivot independently of the elongate support shaft, wherein the support body comprises a plurality of flaps defining a plurality of channels having an inner surface exposed and extending along an outer surface, wherein one or more constriction members are guided via the plurality of flaps;

cinching one or more constriction members so as to constrict the left atrial appendage, wherein the deflector body comprises a plurality of pockets configured to hold the one or more constriction members guided from the plurality of flaps; and delivering the ligature loop from the flexible hoop assembly to the constricted left atrial appendage while the one or more constriction members constricts the left atrial appendage.

9. The method according to claim 8, wherein the constriction member comprises an undeployed configuration and a deployed configuration, wherein in the undeployed configuration the constriction member is received within one of the plurality of channels, wherein in the deployed configuration the constriction member is removed from the flexible hoop assembly and the inner surface remains exposed.

10. The method according to claim 9, wherein the plurality of flaps are configured to fold in the deployed configuration.

11. The method according to claim 8, wherein cinching the constriction member about the left atrial appendage comprises actuating a constriction control member operatively linked to a control mechanism of the ligature delivery system.

12. The method according to claim 8, wherein the flexible hoop assembly comprises a support body coupled with a support frame, and wherein the support frame is biased to hold the flexible hoop assembly in the trailing configuration whereby a free portion of the support body is disposed proximal to the distal portion of the elongate support shaft.

13. The method according to claim 8, wherein the ligature delivery system comprises a suction mechanism, the method further comprising transmitting suction from a suction source to the left atrial appendage of the patient.

14. The method according to claim 13, wherein the suction mechanism comprises a suction pod, the method further comprising drawing tissue of the left atrial appendage of the patient into the suction pod.

* * * * *